US012735729B2

(12) United States Patent
Nakagame

(10) Patent No.: US 12,735,729 B2
(45) Date of Patent: Sep. 15, 2026

(54) METHOD FOR PRODUCING TEREPHTHALIC ACID FROM BIOMASS RESOURCE, AND METHOD FOR PRODUCING POLYESTER FROM BIOMASS RESOURCE

(71) Applicant: SCHOOL JUDICIAL PERSON IKUTOKU GAKUEN, Kanagawa (JP)

(72) Inventor: Seiji Nakagame, Kanagawa (JP)

(73) Assignee: School Judicial Person Ikutoku Gakuen, Kanagawa (JP)

( * ) Notice: Subject to any disclaimer, the term of this patent is extended or adjusted under 35 U.S.C. 154(b) by 354 days.

(21) Appl. No.: 18/275,206

(22) PCT Filed: Feb. 9, 2022

(86) PCT No.: PCT/JP2022/005192

§ 371 (c)(1),
(2) Date: Jul. 31, 2023

(87) PCT Pub. No.: WO2022/172968

PCT Pub. Date: Aug. 18, 2022

(65) Prior Publication Data

US 2024/0110205 A1 Apr. 4, 2024

(30) Foreign Application Priority Data

Feb. 10, 2021 (JP) ................................ 2021-019812

(51) Int. Cl.
*C12P 7/22* (2006.01)
*C12N 15/80* (2006.01)

(52) U.S. Cl.
CPC ................ *C12P 7/22* (2013.01); *C12N 15/80* (2013.01)

(58) Field of Classification Search
CPC .. C12N 1/00; C12N 1/005; C12P 7/44; C08G 63/183
See application file for complete search history.

(56) References Cited

U.S. PATENT DOCUMENTS

| | | | |
|---|---|---|---|
| 10,036,044 | B2 | 7/2018 | Graf et al. |
| 2016/0168599 | A1 | 6/2016 | Graf et al. |

FOREIGN PATENT DOCUMENTS

| | | |
|---|---|---|
| EP | 3778913 | 2/2021 |
| KR | 10-2015-0143296 | 12/2015 |
| WO | 2000/043489 | 7/2000 |
| WO | 2015/093467 | 6/2015 |
| WO | 2019/189651 | 10/2019 |

OTHER PUBLICATIONS

Luo, Z.W. et al., "Biotransformation of p-xylene into terephthalic acid by engineered *Escherichia coli*", Nature Communications, vol. 8, No. 15689, p. 1-8, (2017).

Sastry, K.S.M. et al., "Studies on mycoacia uda & the oil containing almond like odour produced by this fungus", Indian Journal of Experimental Biology, vol. 18, pp. 836-839, (1980).

Junker, F. et al., "Characterization of the p-toluenesulfonate operon tsaMBCD and tsaR in Comamonas testosterone T-2", Journal of Bacteriology, vol. 179, No. 3, pp. 919-927, (1997).

Nakagame, S., "Creation of bio-PET (Polyethylene Terephthalate) from non-edible biomass resources", The memoirs of Experiment and Research Center, Kanagawa Institute of Technology 2017, vol. 22. pp. 123-125, (2018). Manual Translation.

*Primary Examiner* — Tekchand Saidha
(74) *Attorney, Agent, or Firm* — EVAN LAW GROUP LLC

(57) ABSTRACT

An object of the present invention is to provide a method that has less number of steps, improves the yield of terephthalic acid, and can inexpensively produce terephthalic acid from a biomass resource, while reducing the amount of energy consumption, and a method for producing polyester. The method for producing terephthalic acid comprises a step of converting a biomass resource or a compound derived from the biomass resource to p-tolualdehyde with a microbe. The method for producing polyester comprises a step of reacting terephthalic acid produced from a biomass resource with a diol compound to produce polyester.

13 Claims, 5 Drawing Sheets

Specification includes a Sequence Listing.

[Fig. 1]
(a)
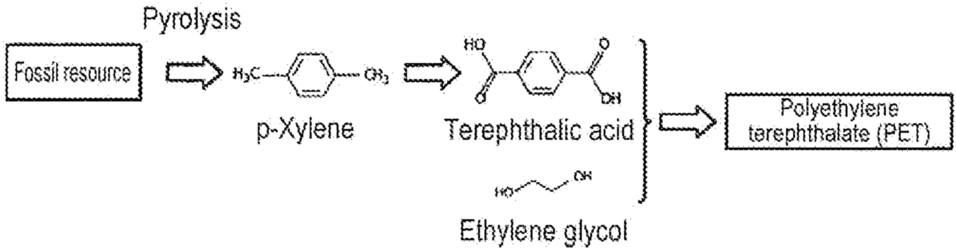
(b)
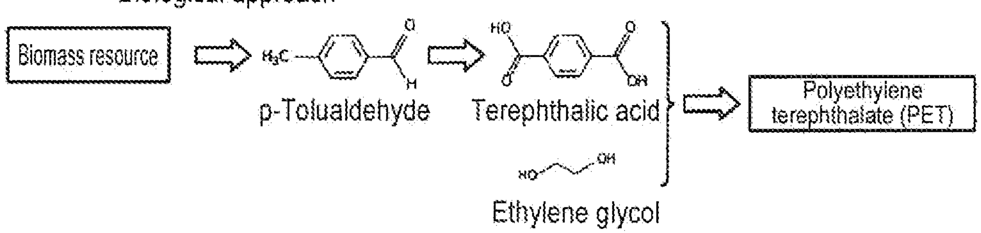

[Fig. 2]
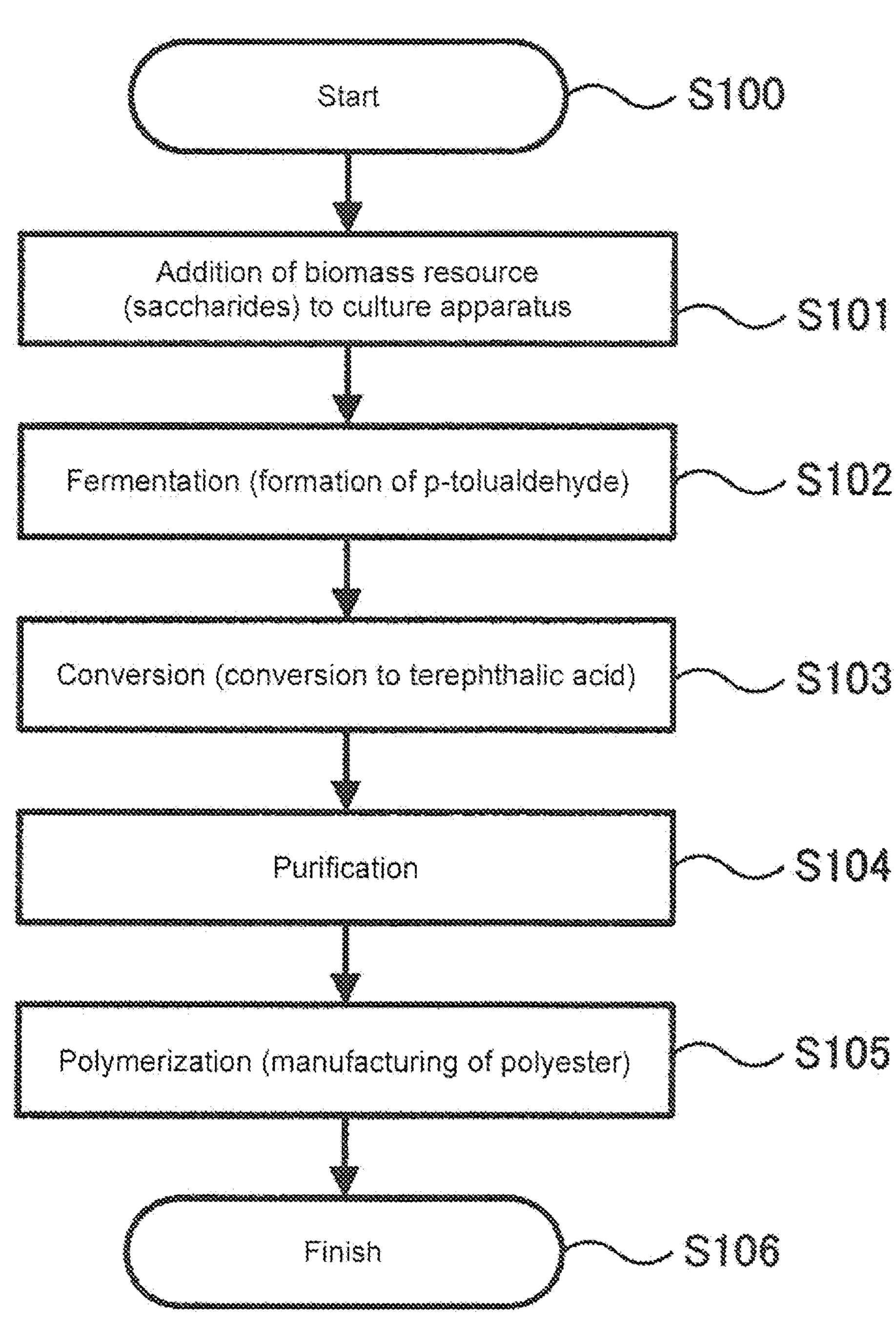

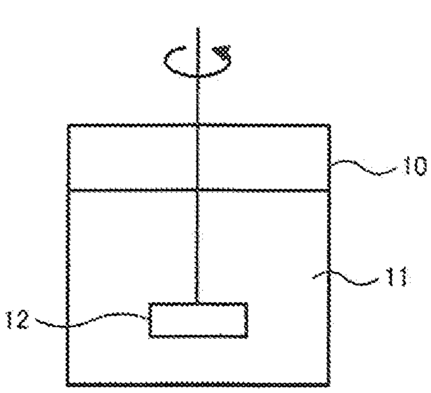
(b)
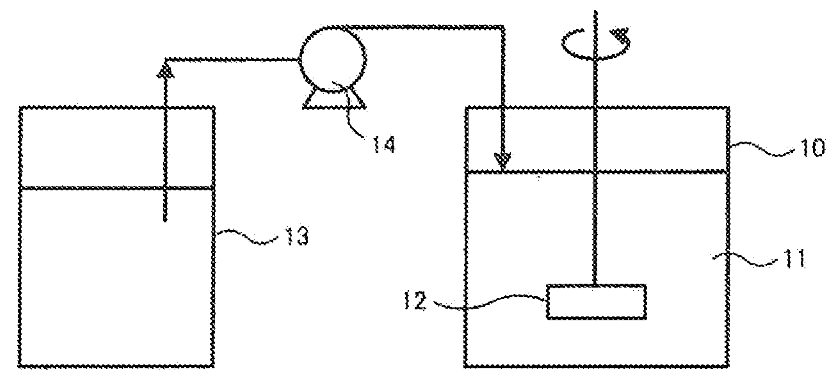
(c)
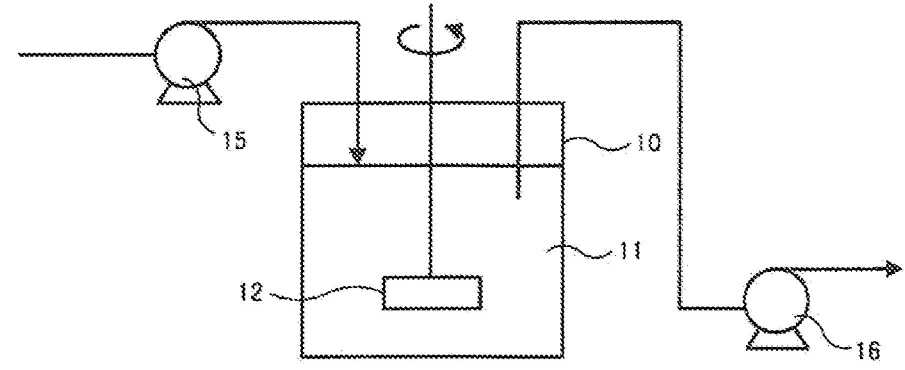

[Fig. 4]
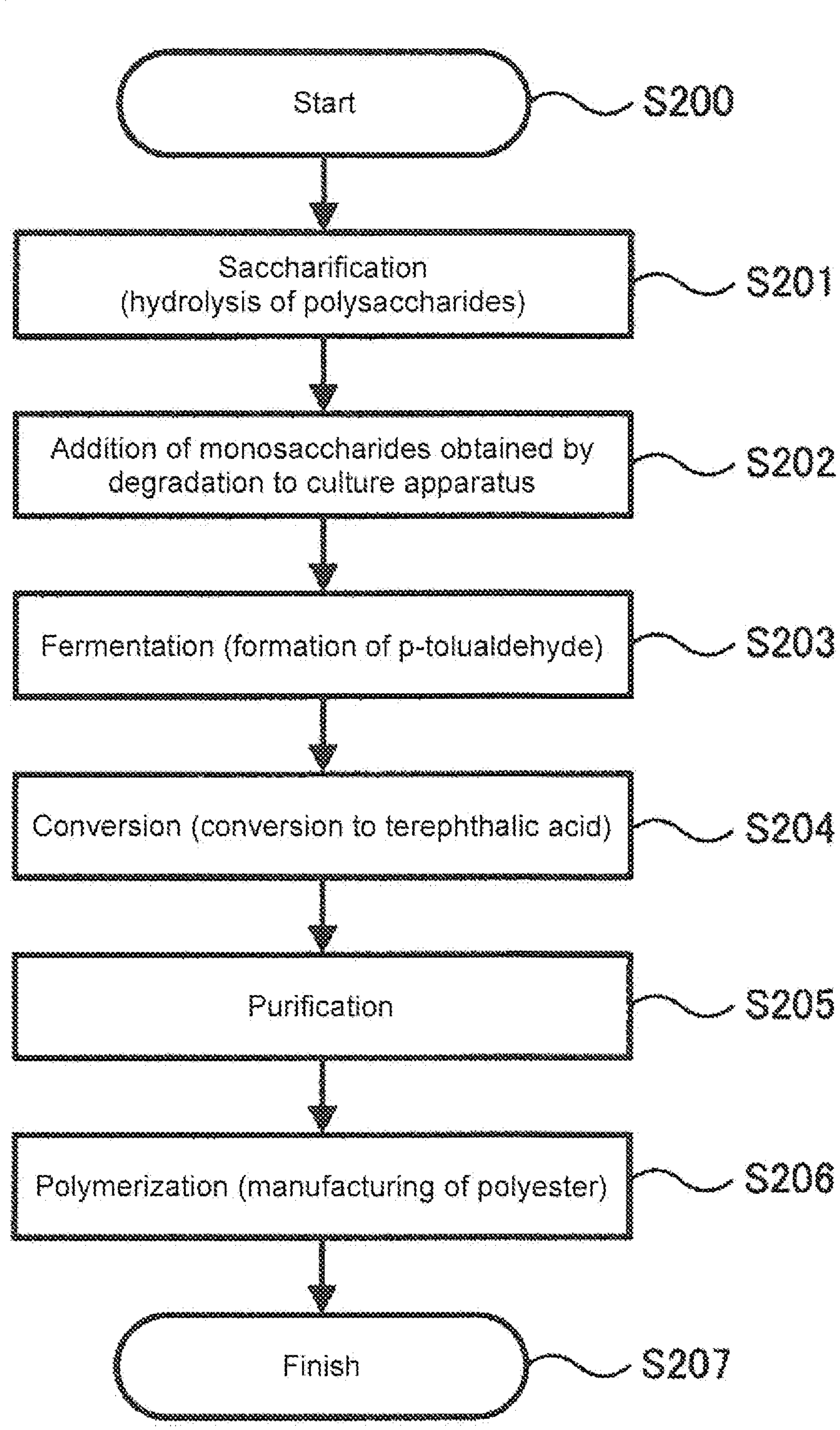

[Fig. 5]

SEQUENCE LISTING

```
<160> NUMBER OF SEQ ID NOS: 23

<210> SEQ ID NO 1
<211> LENGTH: 25
<212> TYPE: DNA
<213> ORGANISM: Artificial
<220> FEATURE:
<223> OTHER INFORMATION: primer 1
<220> FEATURE:
<221> NAME/KEY: misc_feature
<223> OTHER INFORMATION: Inventor: NAKAGAME, Seiji

<400> SEQUENCE: 1

ggtaatttcg acgcacgttc aggcc                                   25
```

<210> SEQ ID NO 2
<211> LENGTH: 32
<212> TYPE: DNA
<213> ORGANISM: Artificial
<220> FEATURE:
<223> OTHER INFORMATION: primer 2

<400> SEQUENCE: 2
cttgcgaaga cggccatgaa aagcaaatga gc 32

<210> SEQ ID NO 3
<211> LENGTH: 32
<212> TYPE: DNA
<213> ORGANISM: Artificial
<220> FEATURE:
<223> OTHER INFORMATION: primer 3

<400> SEQUENCE: 3
gctcatttgc ttttcatggc cgtcttcgca ag 32

<210> SEQ ID NO 4
<211> LENGTH: 32
<212> TYPE: DNA
<213> ORGANISM: Artificial
<220> FEATURE:
<223> OTHER INFORMATION: primer 4

<400> SEQUENCE: 4
ggatgtctaa gacgtgatgc ggataatcgt ag 32

<210> SEQ ID NO 5
<211> LENGTH: 32
<212> TYPE: DNA
<213> ORGANISM: Artificial
<220> FEATURE:
<223> OTHER INFORMATION: primer 5

<400> SEQUENCE: 5
ctacgattat ccgcatcacg tcttagacat cc 32

<210> SEQ ID NO 6
<211> LENGTH: 26
<212> TYPE: DNA
<213> ORGANISM: Artificial
<220> FEATURE:
<223> OTHER INFORMATION: primer 6

<400> SEQUENCE: 6
ctgcgaacgt accgacactt tgatac 26

<210> SEQ ID NO 7
<211> LENGTH: 30
<212> TYPE: DNA
<213> ORGANISM: Artificial
<220> FEATURE:
<223> OTHER INFORMATION: primer 7

<400> SEQUENCE: 7
gttacggatg aacatgaaaa gcaaatgagc 30

<210> SEQ ID NO 8
<211> LENGTH: 30
<212> TYPE: DNA
<213> ORGANISM: Artificial
<220> FEATURE:
<223> OTHER INFORMATION: primer 8

<400> SEQUENCE: 8
gctcatttgc ttttcatgtt catccgtaac 30

<210> SEQ ID NO 9
<211> LENGTH: 30
<212> TYPE: DNA
<213> ORGANISM: Artificial
<220> FEATURE:
<223> OTHER INFORMATION: primer 9

<400> SEQUENCE: 9
ggatgtctaa gacgtaatgt cgaggacaag 30

<210> SEQ ID NO 10
<211> LENGTH: 30
<212> TYPE: DNA
<213> ORGANISM: Artificial
<220> FEATURE:
<223> OTHER INFORMATION: primer 10

<400> SEQUENCE: 10
cttgtcctcg acattacgtc ttagacatcc 30

<210> SEQ ID NO 11
<211> LENGTH: 30
<212> TYPE: DNA
<213> ORGANISM: Artificial
<220> FEATURE:
<223> OTHER INFORMATION: primer 11

<400> SEQUENCE: 11
cttgttgagg ttcatgaaaa gcaaatgagc 30

<210> SEQ ID NO 12
<211> LENGTH: 30
<212> TYPE: DNA
<213> ORGANISM: Artificial
<220> FEATURE:
<223> OTHER INFORMATION: primer 12

<400> SEQUENCE: 12
gctcatttgc ttttcatgaa cctcaacaag 30

<210> SEQ ID NO 13
<211> LENGTH: 30
<212> TYPE: DNA
<213> ORGANISM: Artificial
<220> FEATURE:
<223> OTHER INFORMATION: primer 13

<400> SEQUENCE: 13
ggatgtctaa gacgtaatgt tacgtccgcc 30

<210> SEQ ID NO 14
<211> LENGTH: 30
<212> TYPE: DNA
<213> ORGANISM: Artificial
<220> FEATURE:
<223> OTHER INFORMATION: primer 14

<400> SEQUENCE: 14
ggcggacgta acattacgtc ttagacatcc 30

<210> SEQ ID NO 15

<211> LENGTH: 30
<212> TYPE: DNA
<213> ORGANISM: Artificial
<220> FEATURE:
<223> OTHER INFORMATION: primer 15

<400> SEQUENCE: 15
gagcaccgtg ctcatgaaaa gcaaatgagc 30

<210> SEQ ID NO 16
<211> LENGTH: 30
<212> TYPE: DNA
<213> ORGANISM: Artificial
<220> FEATURE:
<223> OTHER INFORMATION: primer 16

<400> SEQUENCE: 16
gctcatttgc ttttcatgag cacggtgctc 30

<210> SEQ ID NO 17
<211> LENGTH: 31
<212> TYPE: DNA
<213> ORGANISM: Artificial
<220> FEATURE:
<223> OTHER INFORMATION: primer 17

<400> SEQUENCE: 17
ggatgtctaa gacgttgcga cgtagtgcat g 31

<210> SEQ ID NO 18
<211> LENGTH: 31
<212> TYPE: DNA
<213> ORGANISM: Artificial
<220> FEATURE:
<223> OTHER INFORMATION: primer 18

<400> SEQUENCE: 18
catgcactac gtcgcaacgt cttagacatc c 31

<210> SEQ ID NO 19
<211> LENGTH: 492
<212> TYPE: PRT
<213> ORGANISM: Pseudomonas putida
<220> FEATURE:
<221> NAME/KEY: MISC_FEATURE
<223> OTHER INFORMATION: Benzaldehyde dehydrogenase

<400> SEQUENCE: 19

```
Met Ala Val Phe Ala Ser Asp Ser Phe Gly Gln Leu Lys Val Glu Lys
1               5                   10                  15

Ile Met Thr Ala Gln Trp Asn His Tyr Ile Asn Gly Glu Tyr Val Ser
            20                  25                  30

Pro Glu Ser Glu Glu Tyr Ile His Glu Phe Ile Pro Thr Thr Ala Leu
        35                  40                  45

Pro Gly Asp Ser Ile Ala Arg Gly Ser Ala Ala Asp Val Asp Lys Ala
    50                  55                  60

Val Arg Ala Ala Ala Ala Ala Gln Pro Ala Trp Asn Ala Arg Lys Pro
65                  70                  75                  80

Ile Glu Arg Gly Arg Ile Leu Leu Ala Ile Ala Arg Leu Val Arg Ala
                85                  90                  95

Asn Ala Ala Ala Phe Cys Ala Lys Glu Ala Glu Glu Thr Gly Lys Pro
            100                 105                 110

Leu Lys Met Ala Ala Phe Glu Ile Glu Ala Cys Ala Gln Tyr Phe Glu
```

```
        115                 120                 125

Tyr Tyr Gly Gly Leu Ala Thr Ala Ile Gln Gly Glu Thr Ile Asn Leu
    130                 135                 140

Gly Pro Ser Tyr His Ala Tyr Thr Thr Arg Glu Pro Phe Gly Val Val
145                 150                 155                 160

Gly Val Ile Leu Pro Trp Asn Ser Pro Leu Asn Gln Ala Gly Arg Ala
                165                 170                 175

Ile Ala Pro Ala Leu Val Ser Gly Asn Thr Val Val Val Lys Pro Ser
            180                 185                 190

Glu Phe Thr Ser Val Thr Met Leu Gln Phe Ala Glu Leu Val Val Lys
        195                 200                 205

Glu Ala Gly Leu Pro Pro Gly Val Leu Asn Val Val Thr Gly Thr Gly
    210                 215                 220

Lys Glu Thr Gly Glu Pro Leu Val Lys His Pro Leu Ile Arg Lys Val
225                 230                 235                 240

Ala Phe Thr Gly Ser Val Arg Ala Gly Arg Glu Ile Gly Lys Leu Ala
                245                 250                 255

Ala Asp Arg Ile Ile Pro Leu Ser Leu Glu Leu Gly Gly Lys Ser Pro
            260                 265                 270

Asn Ile Val Phe Glu Asp Ala Asp Leu Asp Arg Ala Val Ala Gly Ser
        275                 280                 285

Val Phe Ala Phe Thr Val Asn Thr Gly Gln Val Cys Leu Ala Gly Thr
    290                 295                 300

Arg Cys Leu Val His Glu Ser Ile Phe Glu Lys Phe Ser Lys Lys Leu
305                 310                 315                 320

Ala Gly Ala Val Glu Ala Leu Gln Phe Ser Asp Gly Glu Ser Phe Gly
                325                 330                 335

Leu Gly Pro Leu Thr Thr Lys Ala Gln Phe Glu Gln Val His Arg Tyr
            340                 345                 350

Asn Glu Leu Ala Ile Gln Glu Gly Ala His Cys Leu Val Gly Gly Glu
        355                 360                 365

Ala Pro Ser Asp Lys Thr Gly Trp Tyr Val Arg Pro Thr Val Tyr Thr
    370                 375                 380

Asn Val Asn Asn Ser Met Arg Ile Ala Arg Glu Glu Ile Phe Gly Pro
385                 390                 395                 400

Val Leu Val Leu Ile Pro Phe Lys Asp Glu Asn Glu Ala Val Ala Ile
                405                 410                 415

Ala Asn Asp Ser Asp Tyr Gly Leu Ala Ala Gly Val Trp Thr Thr Asp
            420                 425                 430

Leu Ala Arg Ala His Arg Val Ser Ala Gln Ile Glu Ala Gly Gln Val
        435                 440                 445

Tyr Val Asn Glu Tyr Pro Ser Gly Gly Val Glu Thr Pro Phe Gly Gly
    450                 455                 460

Phe Lys Gln Ser Gly His Gly Arg Glu Lys Gly Ile Glu Ala Leu His
465                 470                 475                 480

His Tyr Thr Gln Thr Lys Thr Thr Ile Ile Arg Ile
                485                 490


<210> SEQ ID NO 20
<211> LENGTH: 663
<212> TYPE: PRT
<213> ORGANISM: Comamonas testosteroni
<220> FEATURE:
<221> NAME/KEY: MISC_FEATURE
<223> OTHER INFORMATION: Toluate methylmonooxygenase
```

```
<400> SEQUENCE: 20

Met Phe Ile Arg Asn Cys Trp Tyr Val Ala Ala Trp Asp Thr Glu Ile
1               5                   10                  15

Pro Ala Glu Gly Leu Phe His Arg Thr Leu Leu Asn Glu Pro Val Leu
            20                  25                  30

Leu Tyr Arg Asp Thr Gln Gly Arg Val Val Ala Leu Glu Asn Arg Cys
        35                  40                  45

Cys His Arg Ser Ala Pro Leu His Ile Gly Arg Gln Glu Gly Asp Cys
    50                  55                  60

Val Arg Cys Leu Tyr His Gly Leu Lys Phe Asn Pro Ser Gly Ala Cys
65                  70                  75                  80

Val Glu Ile Pro Gly Gln Glu Gln Ile Pro Pro Lys Thr Cys Ile Lys
                85                  90                  95

Ser Tyr Pro Val Val Glu Arg Asn Arg Leu Val Trp Ile Trp Met Gly
            100                 105                 110

Asp Pro Ala Arg Ala Asn Pro Asp Asp Ile Val Asp Tyr Phe Trp His
        115                 120                 125

Asp Ser Pro Glu Trp Arg Met Lys Pro Gly Tyr Ile His Tyr Gln Ala
    130                 135                 140

Asn Tyr Lys Leu Ile Val Asp Asn Leu Leu Asp Phe Thr His Leu Ala
145                 150                 155                 160

Trp Val His Pro Thr Thr Leu Gly Thr Asp Ser Ala Ala Ser Leu Lys
                165                 170                 175

Pro Val Ile Glu Arg Asp Thr Thr Gly Thr Gly Lys Leu Thr Ile Thr
            180                 185                 190

Arg Trp Tyr Leu Asn Asp Asp Met Ser Asn Leu His Lys Gly Val Ala
        195                 200                 205

Lys Phe Glu Gly Lys Ala Asp Arg Trp Gln Ile Tyr Gln Trp Ser Pro
    210                 215                 220

Pro Ala Leu Leu Arg Met Asp Thr Gly Ser Ala Pro Thr Gly Thr Gly
225                 230                 235                 240

Ala Pro Glu Gly Arg Arg Val Pro Glu Ala Val Gln Phe Arg His Thr
                245                 250                 255

Ser Ile Gln Thr Pro Glu Thr Glu Thr Thr Ser His Tyr Trp Phe Cys
            260                 265                 270

Gln Ala Arg Asn Phe Asp Leu Asp Asp Glu Ala Leu Thr Glu Lys Ile
        275                 280                 285

Tyr Gln Gly Val Val Val Ala Phe Glu Glu Asp Arg Thr Met Ile Glu
    290                 295                 300

Ala His Glu Lys Ile Leu Ser Gln Val Pro Asp Arg Pro Met Val Pro
305                 310                 315                 320

Ile Ala Ala Asp Ala Gly Leu Asn Gln Gly Arg Trp Leu Leu Asp Arg
                325                 330                 335

Leu Leu Lys Ala Glu Asn Gly Gly Thr Ala Pro Met Ser Ala Asp Val
            340                 345                 350

Pro Val Thr Val Ala Ala Val Arg Ala Val Ala Arg Asp Val Leu Ala
        355                 360                 365

Leu Glu Leu Arg His Ala Asn Gly Gln Pro Leu Pro Gly Ala Ser Ala
    370                 375                 380

Gly Ala His Ile Asp Leu Ala Leu Pro Asn Gly Leu Val Arg Gln Tyr
385                 390                 395                 400

Ser Leu Val Asn Ala Thr Gly Gln Ala Thr Met Asp Cys Tyr Gln Val
```

```
                405                 410                 415

Ala Val Gly Trp Asp Ala Asn Ser Arg Gly Gly Ser Val Trp Ile His
            420                 425                 430

Glu Lys Leu Lys Val Gly Gln Ala Leu Arg Val Thr His Arg Ala Thr
        435                 440                 445

Cys Ser Glu Met Ala Pro Glu His Arg Arg Val Leu Leu Leu Ala Gly
    450                 455                 460

Gly Ile Gly Val Thr Pro Ile Tyr Ala Met Ala Gln Ala Cys Ala Gln
465                 470                 475                 480

Gln Gly Val Asp Val Glu Leu Trp Ala Ser Ala Arg Ser Ala Pro Arg
                485                 490                 495

Leu Ala Tyr Leu Glu Glu Leu Lys Ala Leu Leu Gly Gln Arg Leu His
            500                 505                 510

Leu His Ala Asp Asp Glu Gln Gly Gly Pro Met Asn Leu Thr Glu Arg
        515                 520                 525

Leu Ala Thr Gln Arg Trp Asp Ala Val Tyr Ala Cys Gly Pro Ala Pro
    530                 535                 540

Met Leu Asp Ala Leu Thr Ala Ala Thr Ala His Trp Ala Pro Gly Ser
545                 550                 555                 560

Val Arg Met Glu Arg Phe Lys Gly Ala Glu Gln Pro Ala Ser Glu Arg
                565                 570                 575

Gln Pro Phe Glu Leu Val Leu Gln Arg Ala Gly Leu Ser Thr Thr Val
            580                 585                 590

Asp Ala His Glu Ser Val Leu Asp Ala Met Glu Arg Val Gly Val Asp
        595                 600                 605

Phe Pro Trp Ser Cys Arg Glu Gly Ile Cys Gly Thr Cys Glu Ala Pro
    610                 615                 620

Val Leu Glu Gly Glu Val Gln His Leu Asp Tyr Val Leu Ser Pro Glu
625                 630                 635                 640

Glu Arg Ala Glu Gln Arg Arg Met Met Val Cys Val Ser Arg Cys Gly
                645                 650                 655

Gly Gly Arg Leu Val Leu Asp
            660


<210> SEQ ID NO 21
<211> LENGTH: 252
<212> TYPE: PRT
<213> ORGANISM: Comamonas testosteroni
<220> FEATURE:
<221> NAME/KEY: MISC_FEATURE
<223> OTHER INFORMATION: 4-carboxybenzyl alcohol dehydrogenase

<400> SEQUENCE: 21

Met Asn Leu Asn Lys Gln Val Ala Ile Val Thr Gly Gly Ala Ser Gly
1               5                   10                  15

Phe Gly Ala Ala Ile Ala Arg Arg Leu Ser Gln Ala Gly Ala Ala Val
            20                  25                  30

Leu Val Ala Asp Leu Asn Ala Glu Gly Ala Gln Arg Met Ala Thr Glu
        35                  40                  45

Leu Asn Ala Ala Gly Gly Arg Ala Leu Gly Met Ala Cys Asp Val Ser
    50                  55                  60

Lys Glu Ala Asp Tyr Arg Ala Val Val Asp Ala Ala Ile Ala Gln Leu
65                  70                  75                  80

Gly Gly Leu His Ile Val Val Asn Asn Ala Gly Thr Thr His Arg Asn
                85                  90                  95
```

```
Lys Pro Ala Leu Ala Val Thr Glu Asp Glu Phe Asp Arg Val Tyr Arg
            100                 105                 110

Val Asn Leu Lys Ser Val Tyr Trp Ser Ala Gln Cys Ala Leu Pro His
        115                 120                 125

Phe Ala Gln Gln Gly His Gly Val Met Val Asn Val Ala Ser Thr Thr
    130                 135                 140

Gly Val Arg Pro Gly Pro Gly Leu Thr Trp Tyr Ser Gly Ser Lys Ala
145                 150                 155                 160

Ala Met Ile Asn Leu Thr Lys Gly Leu Ala Leu Glu Phe Ala Arg Ser
                165                 170                 175

Gly Val Arg Ile Asn Ala Val Asn Pro Met Ile Gly Glu Thr Pro Met
            180                 185                 190

Met Ala Asp Phe Met Gly Met Glu Asp Thr Pro Ala Asn Arg Glu Arg
        195                 200                 205

Phe Leu Ser Arg Ile Pro Leu Gly Arg Phe Thr Arg Pro Asp Asp Val
    210                 215                 220

Ala Ser Ala Val Ala Phe Leu Ala Ser Asp Asp Ala Ser Phe Leu Thr
225                 230                 235                 240

Gly Val Cys Leu Asp Val Asp Gly Gly Arg Asn Ile
                245                 250


<210> SEQ ID NO 22
<211> LENGTH: 476
<212> TYPE: PRT
<213> ORGANISM: Comamonas testosteroni
<220> FEATURE:
<221> NAME/KEY: MISC_FEATURE
<223> OTHER INFORMATION: 4-carboxybenzaldehyde dehydrogenase

<400> SEQUENCE: 22

Met Ser Thr Val Leu Tyr Arg Cys Pro Glu Leu Leu Ile Gly Gly Glu
1               5                   10                  15

Trp Arg Pro Gly Arg His Glu Gln Arg Leu Val Val Arg Asn Pro Ala
            20                  25                  30

Thr Gly Glu Pro Leu Asp Glu Leu Arg Leu Ala Ser Ala Asp Asp Leu
        35                  40                  45

Gln Leu Ala Leu Gln Thr Thr Gln Gln Ala Phe Glu His Trp Arg Gln
    50                  55                  60

Val Pro Ala His Glu Arg Cys Ala Arg Leu Glu Arg Gly Val Ala Arg
65                  70                  75                  80

Leu Arg Glu Asn Thr Glu Arg Ile Ala His Leu Leu Thr Leu Glu Gln
                85                  90                  95

Gly Lys Thr Leu Ala Glu Ala Arg Met Glu Cys Ala Met Ala Ala Asp
            100                 105                 110

Leu Ile Lys Trp Tyr Ala Glu Glu Ala Arg Arg Val Tyr Gly Arg Val
        115                 120                 125

Ile Pro Ala Arg Leu Pro Asn Ser Arg Met Glu Val Phe Lys Phe Pro
    130                 135                 140

Val Gly Pro Val Ala Ala Phe Ser Pro Trp Asn Phe Pro Leu Val Leu
145                 150                 155                 160

Ser Ala Arg Lys Leu Gly Gly Ala Ile Ala Ala Gly Cys Ser Ile Val
                165                 170                 175

Leu Lys Ala Ala Glu Glu Thr Pro Ala Ser Val Ala Ala Met Val Asp
            180                 185                 190

Cys Leu Asn Gln Glu Leu Pro Pro Gly Val Val Gln Leu Leu Tyr Gly
        195                 200                 205
```

```
Val Pro Ala Glu Val Ser Gln Ala Leu Ile Ala Ser Pro Val Val Arg
    210                 215                 220

Lys Val Thr Phe Thr Gly Ser Val Pro Val Gly Arg His Leu Ala Glu
225                 230                 235                 240

Leu Ser Ala Arg His Leu Lys Arg Ile Thr Leu Glu Leu Gly Gly His
                245                 250                 255

Ala Pro Val Ile Val Cys Gly Asp Ala Asp Ile Ala Arg Thr Val Asn
            260                 265                 270

Leu Met Val Gln His Lys Phe Arg Asn Ala Gly Gln Ala Cys Leu Ala
        275                 280                 285

Pro Thr Arg Phe Phe Val Asp Arg Arg Ile Tyr Gly Asp Phe Val Asp
    290                 295                 300

Ala Phe Gly Ala Thr Gln Ala Leu Arg Val Gly Ala Gly Met Ala Ala
305                 310                 315                 320

Glu Thr Gln Met Gly Pro Val Ala Ser Ala Arg Arg Gln Ala Ala Val
                325                 330                 335

Gln Asp Leu Ile Ala Arg Ser Val Ala Ala Gly Ala Arg Pro Val Ala
            340                 345                 350

Ser Ala Val Pro Glu Ala Gly Tyr Phe Val Ala Pro Thr Leu Leu Ala
        355                 360                 365

Asp Val Pro Leu Asp Ala Pro Val Met Ser Glu Glu Pro Phe Gly Pro
    370                 375                 380

Val Ala Cys Ala Val Pro Phe Asp Ser Leu Asp Gln Ala Ile Ala Gln
385                 390                 395                 400

Ala Asn His Asn Pro Tyr Gly Leu Ala Gly Tyr Leu Phe Thr Asp Ser
                405                 410                 415

Ala Lys Ala Ile Leu Ala Val Ser Glu Arg Leu Glu Val Gly Ser Leu
            420                 425                 430

Ala Val Asn Gly Met Gly Val Ser Val Pro Glu Ala Pro Phe Gly Gly
        435                 440                 445

Val Lys Asp Ser Gly Tyr Gly Ser Glu Ser Gly Thr Glu Gly Met Glu
    450                 455                 460

Ala Phe Leu Asp Thr Lys Phe Met His Tyr Val Ala
465                 470                 475
```

<210> SEQ ID NO 23
<211> LENGTH: 501
<212> TYPE: PRT
<213> ORGANISM: Sphingomonas aromaticivorans
<220> FEATURE:
<221> NAME/KEY: MISC_FEATURE
<223> OTHER INFORMATION: Benzaldehyde dehydrogenase

<400> SEQUENCE: 23

```
Met Ala Thr Gln Leu Arg Ser Ala Glu Asn Glu Tyr Gly Ile Lys Ser
1               5                   10                  15

Glu Tyr Gly His Tyr Ile Gly Gly Glu Trp Ile Ala Gly Asp Ser Gly
            20                  25                  30

Lys Thr Ile Asp Leu Leu Asn Pro Ser Thr Gly Lys Val Leu Thr Lys
        35                  40                  45

Ile Gln Ala Gly Asn Ala Lys Asp Ile Glu Arg Ala Ile Ala Ala Ala
    50                  55                  60

Lys Ala Ala Phe Pro Lys Trp Ser Gln Ser Leu Pro Gly Glu Arg Gln
65                  70                  75                  80

Glu Ile Leu Ile Glu Val Ala Arg Arg Leu Lys Ala Arg His Ser His
```

```
                85                  90                  95

Tyr Ala Thr Leu Glu Thr Leu Asn Asn Gly Lys Pro Met Arg Glu Ser
            100                 105                 110

Met Tyr Phe Asp Met Pro Gln Thr Ile Gly Gln Phe Glu Leu Phe Ala
        115                 120                 125

Gly Ala Ala Tyr Gly Leu His Gly Gln Thr Leu Asp Tyr Pro Asp Ala
    130                 135                 140

Ile Gly Ile Val His Arg Glu Pro Leu Gly Val Cys Ala Gln Ile Ile
145                 150                 155                 160

Pro Trp Asn Val Pro Met Leu Met Met Ala Cys Lys Ile Ala Pro Ala
                165                 170                 175

Leu Ala Ser Gly Asn Thr Val Val Leu Lys Pro Ala Glu Thr Val Cys
            180                 185                 190

Leu Ser Val Ile Glu Phe Phe Val Glu Met Ala Asp Leu Leu Pro Pro
        195                 200                 205

Gly Val Ile Asn Val Val Thr Gly Tyr Gly Ala Asp Val Gly Glu Ala
    210                 215                 220

Leu Val Thr Ser Pro Asp Val Ala Lys Val Ala Phe Thr Gly Ser Ile
225                 230                 235                 240

Ala Thr Ala Arg Arg Ile Ile Gln Tyr Ala Ser Ala Asn Ile Ile Pro
                245                 250                 255

Gln Thr Leu Glu Leu Gly Gly Lys Ser Ala His Ile Val Cys Gly Asp
            260                 265                 270

Ala Asp Ile Asp Ala Ala Val Glu Ser Ala Thr Met Ser Thr Val Leu
        275                 280                 285

Asn Lys Gly Glu Val Cys Leu Ala Gly Ser Arg Leu Phe Leu His Gln
    290                 295                 300

Ser Ile Gln Asp Glu Phe Leu Ala Lys Phe Lys Thr Ala Leu Glu Gly
305                 310                 315                 320

Ile Arg Gln Gly Asp Pro Leu Asp Met Ala Thr Gln Leu Gly Ala Gln
                325                 330                 335

Ala Ser Lys Met Gln Phe Asp Lys Val Gln Ser Tyr Leu Arg Leu Ala
            340                 345                 350

Thr Glu Glu Gly Ala Glu Val Leu Thr Gly Gly Ser Arg Ser Asp Ala
        355                 360                 365

Ala Asp Leu Ala Asp Gly Asn Phe Ile Lys Pro Thr Val Phe Thr Asn
    370                 375                 380

Val Asn Asn Ser Met Arg Ile Ala Gln Glu Glu Ile Phe Gly Pro Val
385                 390                 395                 400

Thr Ser Val Ile Thr Trp Ser Asp Glu Asp Asp Met Met Lys Gln Ala
                405                 410                 415

Asn Asn Thr Thr Tyr Gly Leu Ala Gly Gly Val Trp Thr Lys Asp Ile
            420                 425                 430

Ala Arg Ala His Arg Ile Ala Arg Lys Leu Glu Thr Gly Thr Val Trp
        435                 440                 445

Ile Asn Arg Tyr Tyr Asn Leu Lys Ala Asn Met Pro Leu Gly Gly Tyr
    450                 455                 460
```

-continued

```
Lys Gln Ser Gly Phe Gly Arg Glu Phe Ser His Glu Val Leu Asn His
465                 470                 475                 480

Tyr Thr Gln Thr Lys Ser Val Val Val Asn Leu Gln Glu Gly Arg Thr
                485                 490                 495

Gly Met Phe Asp Gln
            500
```

METHOD FOR PRODUCING TEREPHTHALIC ACID FROM BIOMASS RESOURCE, AND METHOD FOR PRODUCING POLYESTER FROM BIOMASS RESOURCE

TECHNICAL FIELD

The present invention relates to a method for producing terephthalic acid from a biomass resource and a method for producing polyester from a biomass resource.

BACKGROUND ART

Terephthalic acid, a raw material of polyester, is produced by oxidation of p-xylene, which is obtained through a pyrolysis step of naphtha derived from a fossil resource (crude oil), followed by a distillation step. Problems of fossil resources are increase in carbon dioxide emissions responsible for global warming during combustion, in addition to possible future depletion.

On the other hand, biomass resources can fix carbon dioxide in the atmosphere by photosynthesis, in addition to being renewable resources. Therefore, terephthalic acid and polyester produced from biomass resources are expected to reduce carbon dioxide emissions as compared with terephthalic acid and polyester obtained from fossil resources as raw materials. Hence, methods for producing terephthalic acid and polyester from biomass resources have been proposed (see, for example, patent documents 1 to 3 and non-patent documents 1 to 3).

Polyester is excellent in mechanical strength, chemical stability, and transparency and is inexpensive, and as such, is a synthetic resin that is most frequently used worldwide as various fibers, films, sheets, containers, and the like. Polyester is a polymer compound obtained by the polycondensation of polyvalent carboxylic acid and a polyhydric alcohol. Polyester obtained using terephthalic acid as the polyvalent carboxylic acid includes polyethylene terephthalate (PET), polytrimethylene terephthalate (PTT), polybutylene terephthalate (PBT), polybutylene adipate terephthalate (PEAT), polybutylene terephthalate succinate (PETS), and the like. PET is utilized in fibers, PET bottles, films, and the like. PTT is utilized in fibers and the like, and PBT is utilized in injection-molded parts and the like. PBAT and PETS are utilized as biodegradable polymers.

PRIOR ART DOCUMENTS

Patent Documents

Patent Document 1: Japanese unexamined Patent Application Publication No. 2014-1257

Patent Document 2: Japanese unexamined Patent Application Publication No. 2015-193647

Patent Document 3: International Publication No. WO 2013/111782

Non-Patent Documents

Non-patent Document 1: "Decided to construct pilot plants in the USA toward the development of 100% plant-based PET bottles", [online: Suntory Holdings Ltd., Suntory Beverage & Food Ltd. [searched on Dec. 15, 2020: Internet <URL: https://www.suntory.co.jp/news/article/12563.html>

Non-patent Document 2: "Toray's 100% plant-based synthetic fibers" [online: Nikkei Inc., [searched on Dec. 15, 2020: Internet <URL: https://www.nikkei.com/nkd/company/article/?DisplayType=1&ng=DGKKZO55934740R20C20A2TJC000&scode=3401&ba=1>

Non-patent Document 3: "Developed a method for making raw materials of PET resins from biomass resources unsuitable for food" [online: Japan Science and Technology Agency (JST), Gunma University, [searched on Dec. 15, 2020: Internet <URL: https://www.jst.go.jp/pr/announce/20150204/index.html>

SUMMARY OF THE INVENTION

Object to be Solved by the Invention

Although there are disclosed methods for producing terephthalic acid using biomass resources as raw materials and methods for producing polyester using terephthalic acid produced from biomass resources, as described above, all of these methods disadvantageously have a large amount of energy consumption at the time of producing terephthalic acid, and a large number of steps.

As for the amount of energy consumption at the time of producing terephthalic acid, methods described in patent documents 1 to 3 and non-patent documents 1 to 3 described above disadvantageously have a large amount of energy consumption because the methods include a pyrolysis reaction step, a dehydration reaction step, a cyclization reaction step, an aromatization step, and the like at a high temperature of several hundreds of degrees as steps for obtaining p-xylene from a biomass resource. Patent document 3 described above discloses a method for producing p-tolualdehyde from a biomass resource, however, disadvantageously has a large amount of energy consumption because the reaction of an aromatization step is performed at a high temperature of 400° C., as in the description above.

Furthermore, the methods described in patent documents 1 to 3 and non-patent documents 1 to 3 described above disadvantageously have a large number of steps as steps for producing terephthalic acid from a biomass resource. A p-xylene producing method disclosed in patent document 2 requires a lot of equipment and heavy economic burden for chemical conversion because a chemical conversion step is as long as 3 steps. Also, a p-xylene producing step disclosed in patent document 2 needs a lot of equipment and heavy economic burden for chemical conversion because a chemical conversion step has 2 steps. Non-patent document 3 requires a lot of equipment and heavy economic burden, as in the description above, because a chemical conversion step of terephthalic acid from furfural has 5 steps. Patent documents 2 and 3, which disclose a method for producing p-xylene from a biomass resource, require at least one additional chemical conversion step for producing terephthalic acid.

Means to Solve the Object

As a result of conducting diligent studies in light of the problems described above, the present invention has found that a method for producing terephthalic acid, comprising a step of converting a biomass resource or a compound derived from the biomass resource to p-tolualdehyde with a microbe through a short step in a low amount of energy consumption, and a method for producing polyester. It has also been confirmed that when a transformant obtained by transfecting a microbe that produces p-tolualdehyde with a gene group encoding four types of enzymes, benzaldehyde dehydrogenase, toluate methylmonooxygenase, 4-carboxybenzyl alcohol dehydrogenase, and 4-carboxybenzaldehyde dehydrogenase, is used, terephthalic acid can be biotransformed from p-tolualdehyde formed in the transformant. The present invention has been completed on the basis of these findings.

Specifically, the present invention is as follows.

[1] A method for producing terephthalic acid, comprising a step of converting a biomass resource or a compound derived from the biomass resource to p-tolualdehyde with a microbe.

[2] The method for producing terephthalic acid according to [1] above, wherein the compound derived from the biomass resource is at least one of shikimic acid, 1-p-tolyl ethanol, p-methylacetophenone, and p-methylbenzyl alcohol.

[3] The method for producing terephthalic acid according to [1] or [2] above, wherein the biomass resource is a biomass resource treated by a pretreatment step or a saccharification step or both steps.

[4] The method for producing terephthalic acid according to any one of [1] to [3] above, wherein the biomass resource is any one or more of edible biomass, edible biomass-derived monosaccharides or polysaccharides, inedible biomass, and inedible biomass-derived monosaccharides or polysaccharides.

[5] The method for producing terephthalic acid according to [4] above, wherein the edible biomass comprises at least one type of biomass selected from maize, sweet potato, rice, potato, wheat, barley, tapioca, sugar cane, beet, molasses, and high-test molasses.

[6] The method for producing terephthalic acid according to [4] above, wherein the inedible biomass comprises at least one type of biomass selected from grass biomass, wood biomass, paper, pulp, waste paper, bagasse, and corn stover.

[7] The method for producing terephthalic acid according to any one of [1] to [6] above, further comprising a step of adding at least one type of enzyme selected from amylase, cellulase, hemicellulase, and ligninolytic enzyme to a medium.

[8] The method for producing terephthalic acid according to any one of [1] to [7] above, wherein the p-tolualdehyde is biologically oxidized by use of a microbe to produce terephthalic acid.

[9] The method for producing terephthalic acid according to [8] above, wherein the microbe is the same as that employed in the formation of p-tolualdehyde and is a microbe transfected with a gene group encoding four types of enzymes, benzaldehyde dehydrogenase, toluate methylmonooxygenase, 4-carboxybenzyl alcohol dehydrogenase, and 4-carboxybenzaldehyde dehydrogenase.

[10] The method for producing terephthalic acid according to any one of [1] to [9] above, wherein the microbe is *Phlebia uda* or *Hydnophlebia chrysorhiza*.

[11] A method for producing polyester, comprising a step of reacting terephthalic acid produced by a method for producing terephthalic acid according to any one of [1] to [10] above with a diol compound to produce polyester.

[12] A microbe transfected with a gene group encoding four types of enzymes, benzaldehyde dehydrogenase, toluate methylmonooxygenase, 4-carboxybenzyl alcohol dehydrogenase, and 4-carboxybenzaldehyde dehydrogenase, the microbe being capable of producing p-tolualdehyde from a biomass resource or a compound derived from the biomass resource (hereinafter, also referred to as the "present microbe").

[13] The microbe according to [12] above, wherein
the benzaldehyde dehydrogenase has at least 90% sequence identity to the amino acid sequence represented by SEQ ID NO: 19, and retains benzaldehyde dehydrogenase activity,
the toluate methylmonooxygenase has at least 90% sequence identity to the amino acid sequence represented by SEQ ID NO: 20, and retains toluate methylmonooxygenase activity,
the 4-carboxybenzyl alcohol dehydrogenase has at least 90% sequence identity to the amino acid sequence represented by SEQ ID NO: 21, and retains 4-carboxybenzyl alcohol dehydrogenase activity, and
the 4-carboxybenzaldehyde dehydrogenase has at least 90% sequence identity to the amino acid sequence represented by SEQ ID NO: 22, and retains 4-carboxybenzaldehyde dehydrogenase activity.

[14] The microbe according to [12] or [13] above, wherein the microbe is *Phlebia uda* or *Hydnophlebia chrysorhiza*.

[15] A method for preparing a microbe transfected with a gene group encoding four types of enzymes, benzaldehyde dehydrogenase, toluate methylmonooxygenase, 4-carboxybenzyl alcohol dehydrogenase, and 4-carboxybenzaldehyde dehydrogenase, comprising a step of transfecting a microbe with the gene group, wherein the microbe is a microbe capable of producing p-tolualdehyde from a biomass resource or a compound derived from the biomass resource (hereinafter, also referred to as the "present microbe preparation method").

[16] The method according to [15] above, wherein
the benzaldehyde dehydrogenase has at least 90% sequence identity to the amino acid sequence represented by SEQ ID NO: 19, and retains benzaldehyde dehydrogenase activity,
the toluate methylmonooxygenase has at least 90% sequence identity to the amino acid sequence represented by SEQ ID NO: 20, and retains toluate methylmonooxygenase activity,
the 4-carboxybenzyl alcohol dehydrogenase has at least 90% sequence identity to the amino acid sequence represented by SEQ ID NO: 21, and retains 4-carboxybenzyl alcohol dehydrogenase activity, and
the 4-carboxybenzaldehyde dehydrogenase has at least 90% sequence identity to the amino acid sequence represented by SEQ ID NO: 22, and retains 4-carboxybenzaldehyde dehydrogenase activity.

[17] The method according to [15] or [16] above, wherein the microbe is *Phlebia uda* or *Hydnophlebia chrysorhiza*.

Effect of the Invention

According to the present invention, a biomass resource can be converted to p-tolualdehyde at ordinary temperature by use of a fermentation method using a microbe. Therefore, the amount of energy consumption can be drastically reduced. Furthermore, in the present invention, p-tolualdehyde having the same carbon skeleton as that of terephthalic acid can be produced through one step by microbial fermentation from a biomass resource. Therefore, the number of steps can be decreased in producing terephthalic acid. Moreover, when a transformant obtained by transfecting a microbe that produces p-tolualdehyde with a gene group encoding four types of enzymes, benzaldehyde dehydrogenase, toluate methylmonooxygenase, 4-carboxybenzyl alcohol dehydrogenase, and 4-carboxybenzaldehyde dehydrogenase, is used, terephthalic acid can be biotransformed from p-tolualdehyde formed in the transformant. Therefore, terephthalic acid can be produced by one step from a biomass resource, and the amount of energy consumption can be drastically reduced. Hence, the cost of equipment can be reduced, and economic burden is small, as compared with other methods known in the art. Besides, it is also possible to provide a method for producing polyester produced by this method.

BRIEF DESCRIPTION OF DRAWINGS

FIG. 1 A diagram illustrating the outline of methods for producing terephthalic acid and polyester.

FIG. 2 A diagram showing a first example of a producing flow of terephthalic acid and polyester.

FIG. 3 A diagram showing a configuration example of a culture apparatus.

FIG. 4 A diagram showing a second example of a second production flow of terephthalic acid and polyester.

FIG. 5 A diagram showing a third example of a third production flow of terephthalic acid and polyester.

MODE OF CARRYING OUT THE INVENTION

The outline of methods for producing terephthalic acid and polyester will be described with reference to FIG. 1. FIG. 1(*a*) is a diagram illustrating a conventional method, and FIG. 1(*b*) is a diagram illustrating the method of the present invention. Here, the production of polyethylene terephthalate (PET) as one example of polyester will be described.

In the conventional method, a fossil resource such as crude oil is employed as a raw material of terephthalic acid. Naphtha or the like obtained by purifying crude oil is used as a raw material, pyrolyzed at a high temperature, and fractionated with a fractionator to obtain p-xylene as an intermediate product. The p-xylene is oxidized by the supply of air in the presence of a catalyst such as cobalt, manganese, or bromine to produce terephthalic acid.

The produced terephthalic acid is dissolved in ethylene glycol formed from ethylene, and polycondensed to produce polyethylene terephthalate (PET).

On the other hand, the method of the present invention employs a biomass resource or a compound derived from the biomass resource, not a fossil resource, as a raw material. Specifically, the method of the present invention comprises a step of culturing a microbe in the presence of a biomass resource or a compound derived from the biomass resource. The culture can be performed, for example, by solid-culturing the microbe on biomass; leaving the microbe standing on a culture medium solidified with agar, gellan gum, agarose, or the like; and/or leaving the microbe standing in a liquid culture medium or shaking the microbe in a liquid culture medium. Also, the culture can be performed under conditions such as an appropriate culture medium, an appropriate culture temperature, and an appropriate culture period. The culture medium is not particularly limited as long as the medium permits growth and proliferation of the microbe. Examples thereof can include potato dextrose agar (FDA) medium, malt extract agar (MA) medium, LB agar medium, LB liquid medium, YM liquid medium, and TB liquid medium.

The culture temperature is not particularly limited and is, for example, in the range of 15 to 40° C., preferably 20 to 38° C., more preferably 22 to 30° C., further preferably 24 to 28° C.

The culture period is not particularly limited and is, for example, in the range of 4 to 40 days, preferably 5 to 35 days, more preferably 5 to 30 days, further preferably 10 to 20 days.

In the case of culturing the microbe under shaking conditions, the shaking rate is, for example, in the range of 60 to 300 rpm, preferably 80 to 120 rpm.

The microbe degrades or alters the biomass resource or the compound derived from the biomass resource by its own enzyme to form p-tolualdehyde having the same carbon skeleton as that of terephthalic acid as an intermediate product. Thus, another embodiment of the present invention can include a method for forming p-tolualdehyde, comprising a step of culturing a microbe in the presence of a biomass resource or a compound derived from the biomass resource. After implementation of this formation method, the culture solution containing p-tolualdehyde can be heated and then cooled in a condenser or the like co recover a solution containing p-tolualdehyde. Also, an emission gas from a culture vessel where the microbe is cultured can be cooled using a condenser or the like to recover p-tolualdehyde while performing culture. p-Tolualdehyde can be recovered from the culture solution containing p-tolualdehyde by extraction with an organic solvent. The organic solvent can be of any type as long as the organic solvent is not completely miscible with water. For example, petroleum ether, hexane, ethyl acetate, chloroform, or 4-methyltetrahydropyran can be utilized. Such an organic solvent may be added at the time of culture without largely inhibiting the growth of the microbe. A purification method such as chromatography or distillation can be used for increasing p-tolualdehyde into a desired concentration. Then, the obtained p-tolualdehyde is oxidized to produce terephthalic acid. In this respect, the oxidation may be chemically performed by the supply of air as described above. A method of biologically oxidizing the p-tolualdehyde using a microbe (preferably the same microbe as that employed in the formation of p-tolualdehyde) is preferred from the viewpoint of producing terephthalic acid in a low amount of energy consumption and through a short step. In the case of biologically oxidizing p-tolualdehyde into terephthalic acid, the p-tolualdehyde after purification by the method described above may be oxidized into terephthalic acid, or the p-tolualdehyde may be oxidized into terephthalic acid by coculturing the microbe that forms p-tolualdehyde and the microbe that oxidizes p-tolualdehyde into terephthalic acid.

Examples of the method for biologically oxidizing p-tolualdehyde by use of a microbe can include a method of biotransforming terephthalic acid from the p-tolualdehyde formed in the microbe through chemical reactions shown in formulas (I) to (IV) given below. In the case of producing terephthalic acid by use of this method, the microbe preferably expresses four types of enzymes (benzaldehyde dehydrogenase [BZDH] which catalyzes a chemical reaction shown in the following formula (I); toluate methylmonooxygenase [TsaMB] which catalyzes a chemical reaction shown in the following formula (II); 4-CBAL dehydrogenase [TsaC] which catalyzes a chemical reaction shown in the following formula (III); and 4-CBA dehydrogenase [TsaD] which catalyzes a chemical reaction shown in the following formula (IV)) (document "Nat Commun. 2017 May 31; 8: 15689").

$$\text{p-Tolualdehyde}+NAD^{+}+H_2O \rightarrow \text{p-Toluic acid (pTA)}+NADH+2H^{+} \quad (I)$$

$$\text{pTA}+NADH+O_2+H^{+} \rightarrow \text{4-Carboxybenzyl alcohol (4-CBAL)}+NAD^{+}+H_2O \quad (II)$$

$$\text{4-CBAL}+NAD^{+}+H_2O \rightarrow \text{4-Carboxybenzaldehyde (4-CBA)}+NADH+2H^{+} \quad (III)$$

$$\text{4-CBA}+NAD^{+}+H_2O \rightarrow \text{Terephthalic acid}+NADH+2H^{+} \quad (IV)$$

When the microbe is not a microbe expressing the four types of enzymes (BZDH, TsaMB, TsaC, and TsaD), a microbe transfected with a gene group encoding the four types of enzymes is preferred, the microbe being capable of producing p-tolualdehyde from a biomass resource or a compound derived from the biomass resource (i.e., the present microbe). The present microbe can be obtained by a method comprising a step of transfecting a microbe with a gene (polynucleotide) group encoding the four types of enzymes, the microbe being capable of producing p-tolualdehyde from a biomass resource or a compound derived from the biomass resource (i.e., the present microbe preparation method). Examples of the transfection method can include a method using a calcium ion, general competent cell transformation, protoplast transformation, and electroporation.

More specifically, the gene group encoding the four types of enzymes to transfect the microbe is contained in a vector (wherein the respective genes may be contained in the same vector or separate vectors) in which a promoter is operably linked upstream thereof. The vector may further contain an enhancer region or the base sequence of a ribosome binding site (RBS) in order to further enhance gene expression efficiency, or may further contain a drug resistance gene (selective marker gene) such as carboxin resistance gene, spectinomycin resistance gene, chloramphenicol resistance gene, tetracycline resistance gene, kanamycin resistance gene, or ampicillin resistance gene for screening for a transformed strain. The enhancer region is usually placed upstream of the promoter, and the RBS is usually placed between the promoter and the gene group encoding the four types of enzymes.

In the present specification, the term "promoter" means a region to which RNA polymerase (preferably RNA polymerase and basal transcription factors) binds so that the transcription of mRNA encoded by the gene positioned downstream thereof is started.

The origins of the genes encoding the four types of enzymes are not particularly limited. Examples of the gene encoding BZDH can include a gene encoding *Pseudomonas putida*-derived BZDH (preferably a polypeptide that has at least 90% sequence identity to the amino acid sequence of SEQ ID NO: 19, and retains benzaldehyde dehydrogenase activity [specifically, activity of catalyzing a chemical reaction shown in formula (I) above]), a gene encoding *Novosphingobium* (*Sphingomonas*) *aromaticivorans*-derived BZDH (preferably a polypeptide that has at least 90% sequence identity to the amino acid sequence of SEQ ID NO: 23, and retains benzaldehyde dehydrogenase activity [specifically, activity of catalyzing a chemical reaction shown in formula (I) above)], and orthologs of these genes. Examples of the gene encoding TsaMB can include a gene encoding *Comamonas testosteroni*-derived TsaMB (preferably a polypeptide that has at least 90% sequence identity to the amino acid sequence of SEQ ID NO: 20, and retains toluate methylmonooxygenase activity [specifically, activity of catalyzing a chemical reaction shown in formula (II) above]), and an ortholog of this gene. Examples of the gene encoding TsaC can include a gene encoding *Comamonas testosteroni*-derived TsaC (preferably a polypeptide that has at least 90% sequence identity to the amino acid sequence of SEQ ID NO: 21, and retains 4-carboxybenzyl alcohol dehydrogenase activity [specifically, activity of catalyzing a chemical reaction shown in formula (III) above]), and an ortholog of this gene. Examples of the gene encoding TsaD can include a gene encoding *Comamonas testosteroni*-derived TsaD (preferably a polypeptide that has at least 90$ sequence identity to the amino acid sequence of SEQ ID NO: 22, and retains 4-carboxybenzaldehyde dehydrogenase activity [specifically, activity of catalyzing a chemical reaction shown in formula (IV) above]), and an ortholog of this gene.

For the nucleotide sequences of the genes encoding the four types of enzymes, those skilled in the art can specifically and clearly grasp nucleotide sequences that correspond to the amino acid sequences of the four types of enzymes with reference to the amino acid sequences of the four types of enzymes and codon tables known in the art that correspond to various microbes.

A conventional method can be used as a method for producing polyethylene terephthalate (PET) from terephthalic acid. The ethylene glycol that can be used in the present invention may be ethylene glycol derived from a fossil resource. It is desirable to use bio-ethylene glycol derived from bioethanol produced from a biomass resource, for reducing carbon dioxide emissions causative of global warming.

Thus, the method of the present invention produces terephthalic acid by employing a biomass resource as a raw material and utilizing the culture of a microbe, and as such, eliminates the need of performing conventional reactions, such as pyrolysis, at a high temperature and can drastically reduce the amount of energy consumption. Furthermore, terephthalic acid and polyester can be inexpensively produced because of no need of an expensive apparatus such as a furnace for performing pyrolysis.

Hereinafter, the method of the present invention will be described in detail with reference to the drawings. FIG. 2 is a diagram showing a first example of a production flow of terephthalic acid and polyester. In the example shown in FIG. 2, edible biomass containing saccharides is employed as the biomass resource, and saccharides are employed as the compound derived from the biomass resource. The edible biomass is a biomass resource that grows by photosynthesis and is a biomass resource that can be eaten (for food). The saccharides are monosaccharides or disaccharides which are nutrients serving as energy sources of organisms, and include, for example, glucose, fructose, galactose, mannose, arabinose, xylose, sucrose, and maltose. The saccharides may include oligosaccharides.

Examples of the edible biomass rich in saccharides can include, but are not particularly limited to, sugar cane, grape, beet, molasses, and high-test molasses. Only any one type of edible biomass containing saccharides described above may be employed, or two or more types thereof may be employed.

Starting from step 100, in step 101, edible biomass containing saccharides is added to a culture apparatus where a microbe is cultured. The culture apparatus includes a reaction vessel having a medium for microbe culture. Then, the culture apparatus or a medium component may be sterilized with an autoclave, vapor, or the like. The culture apparatus may be supplemented with biomass resource-derived shikimic acid, 1-p-tolyl ethanol, p-methylacetophenone, or p-methylbenzyl alcohol, in addition to the edible biomass containing saccharides. As for the method for producing p-methylacetophenone from a biomass resource, the p-methylacetophenone can be produced by the microbial fermentation of biomass resource-derived saccharides according to the present invention or can be prepared by the oxidation of citral contained in a biomass resource citrus such as lemon.

In step 102, the microbe in the culture apparatus forms p-tolualdehyde from the saccharides contained in the edible biomass. The microbe forms, from the saccharides, an intermediate product such as p-tolualdehyde shown in FIG. 1(*b*), which is different from the saccharides. This is called fermentation.

The microbe to be cultured may be any microbe as long as the microbe can form p-tolualdehyde from the saccharides. Shikimic acid, 1-p-tolyl ethanol, p-methylacetophenone, or p-methylbenzyl alcohol may also be added to the culture apparatus.

The microbe that can be used in the present invention is not particularly limited as long as the microbe has the ability to form p-tolualdehyde with the biomass resource or the compound derived from the biomass resource as a raw material. Specific examples thereof can include a microbe belonging to the family Meruliaceae. Examples of the microbe belonging to the family Meruliaceae can include microbes belonging to the genus *Abortiporus*, the genus *Amaurohydnum*, the genus *Amauromyces*, the genus *Aquascypha*, the genus *Aurantiopileus*, the genus *Aurantiporus*, the genus *Bjerkandera*, the genus *Bulbillomyces*, the genus *Ceriporiopsis*, the genus *Cerocorticum*, the genus *Chrysoderma*, the genus *Climacodon*, the genus *Columnodontia*, the genus *Conohypha*, the genus *Coralloderma*, the genus *Crustoderma*, the genus *Crustodontia*, the genus *Cyanodontia*, the genus *Cymatoderma*, the genus *Diacanthodes*, the genus *Elaphroporia*, the genus *Gyrophanopsis*, the genus *Hydnophlebia*, the genus *Hyphoderma*, the genus *Hyphodontiastra*, the genus *Hypochnicium*, the genus *Irpex*, the genus *Lilaceophlebia*, the genus *Luteoporia*, the genus *Merulius*, the genus *Mycoacia*, the genus *Mycoaciella*, the genus *Mycoleptodonoides*, the genus *Niemelaea*, the genus *Odoria*, the genus *Phlebia*, the genus *Phlebiporia*, the genus *Pirex*, the genus *Podoscypha*, the genus *Radulodon*, the genus *Sarcodontia*, the genus *Scopuloides*, the genus *Stegiacantha*, and the genus *Uncobasidium*. A microbe belonging to the genus *Phlebia* (e.g., *Phlebia albida, Phlebia aurea, Phlebia brevispora, Phlebia centrifuga, Phlebia chrysocreas, Phlebia coccineofulva, Phlebia floridensis, Phlebia hydnoidea, Phlebia lindtneri, Phlebia lividina, Phlebia ludoviciana, Phlebia nantahaliensis, Phlebia nitidula, Phlebia setulosa, Phlebia subochracea*, and *Phlebia uda*) or a microbe belonging to the genus *Hydnophlebia* (e.g., *Hydnophlebia alachuana, Hydnophlebia canariensis, Hydnophlebia gorgonea, Hydnophlebia meloi, Hydnophlebia ominivora, Hydnophlebia sinensis, Hydnophlebia subchrysorhiza*, and *Hydnophlebia chrysorhiza*) is preferred. Preferred examples thereof can include *Phlebia uda* (which corresponds to "*Mycoacia uda*" employed in the present Example) and *Hydnophlebia chrysorhiza*. These microbes can be obtained by isolation from the natural world. The microbes are also available from ATCC (American Type Culture Collection) or the like. A highly p-tolualdehyde-producing strain may be made by the physical or chemical mutagenesis of such a microbe, and the highly p-tolualdehyde-producing strain thus made can be used.

As for the method for culturing the microbe, the culture can be performed using a fermentation method known in the art such as a batch culture method, a feeding culture method, or a continuous culture method. The p-tolualdehyde obtained by the culture of the microbe can be purified to enhance its purity, before being converted to terephthalic acid. Any method can be used as a method for purifying p-tolualdehyde as long as the method enhances the purity of p-tolualdehyde. For example, the method for purifying p-tolualdehyde can be carried out by any one of or two or more in combination of methods of purifying a chemical product, such as solid-liquid separation, distillation, crystallization, decolorizing, and desalting. The purification method may be carried out by use of a separation technique such as membrane separation or chromatography.

The batch culture method is a method of, as shown in FIG. 3(*a*), adding a medium composition into reaction vessel 10 at the start of fermentation, sterilizing a medium component with an autoclave, vapor, or the like, then inoculating the microbe to medium 11, and culturing the microbe while adjusting pH, an oxygen concentration, a temperature, and the like. The reaction vessel 10 is equipped with stirrer 12 for keeping the concentration of the medium 11 or the concentration of dissolved oxygen uniform, and supplying oxygen into the medium. It is desirable to supply sterilized air from the lower part of the reaction vessel 10. In the batch culture method, proliferation and growth stop due to the depletion of a nutrient because the nutrient, such as a carbon source, for the microbe is not further added. Hence, in the batch culture method, the microbe finally enters a stationary phase where a growth rate decreases or stops through a logarithmic phase from an inductive phase.

The inductive phase is a stage where the microbe is not acclimatized to an environment, and is a period where proliferation rarely occurs. For shortening the time of the inductive phase, it is desirable to increase the amount of the microbe by placing the microbe in advance under appropriate conditions for proliferation as preculture, and then add several % of a medium containing the microbe. The logarithmic phase is a period where the proliferation of the microbe occurs exponentially or logarithmically. The carbon source is, for example, saccharides contained in edible biomass or shikimic acid added into the reaction vessel. The microbial cells thus cultured can be aseptically recovered and thereby employed in subsequent batch culture.

The feeding culture method is a method of gradually adding a carbon source as a fermentation process progresses. Hence, the feeding culture method involves, as shown in FIG. 3(*b*), reservoir 13 for storing a carbon source, and pump 14 which supplies the carbon source from the reservoir 13 to reaction vessel 10. The feeding culture method tends to suppress the metabolism of the microbe by catabolite repression and is a method that is useful when limitations on the amount of a carbon source in a medium are preferred. In this context, the catabolite repression is a phenomenon in which the synthesis rate of a particular enzyme is decreased due to a carbon source added to a medium.

The continuous culture method is a method of continuously supplying a predetermined amount of a medium to a reaction vessel at a constant rate, while withdrawing the same amount thereas of a culture solution. Hence, the continuous culture method involves, as shown in FIG. 3(*c*), pump 15 which supplies medium 11, and pump 16 which withdraws a culture solution from reaction vessel 10. In the continuous culture method, a nutrient can be resupplied by the continuous replacement of a portion or the whole of the medium, and the accumulation of metabolism by-products or dead cells which may adversely affect the growth of the microbe can be prevented.

The microbe used in the present invention can be fixed using a method known in the art such as a carrier binding method, a cross-linking method, or an inclusion method, and utilized. For example, an aerated stirring-type culture vessel, an airlift-type culture vessel, a packed bed-type culture vessel, or a fluidized bed-type culture vessel can be used as the culture apparatus used in the present invention.

The nutrient for use in the culture of the microbe may include not only a carbon source but a nitrogen source, various salts, a vitamin, a mineral, and the like. Examples of the nitrogen source can include a nitrogen compound such as a yeast extract, peptone, various amino acids, soymeal, corn steep liquor, urea, and various inorganic nitrogens.

In step 103, terephthalic acid is produced from p-tolualdehyde. Terephthalic acid is produced from p-tolualdehyde by a chemical oxidation method or a biological oxidation method. Examples of the chemical oxidation method can include a method of performing oxidation with an oxygen-containing gas using a heavy metal salt or a bromine compound as a catalyst (see, for example, Japanese unexamined Patent Application Publication No. 51-86437). Examples of the biological oxidation method can include a method using genetically manipulated *E. coli* (see, for example, Luo, Z., Lee, S. Biotransformation of p-xylene into terephthalic acid by engineered *Escherichia coli*. Nat Commom 8, 15689 (2017) (http://doi.org/10.1038/ncomms15689)).

In step 104, terephthalic acid is purified in order to improve the purity of the terephthalic acid. The purification method can be carried out by any one of or two or more in combination of methods of purifying a chemical product, such as solid-liquid separation, distillation, crystallization, decolorizing, and desalting. The purification method may be carried out by use of a separation technique such as membrane separation or chromatography.

In step 105, the purified terephthalic acid and a diol compound are polymerized to produce polyester. The operation finishes in step 106. The polyester to be produced is polyethylene terephthalate (PET), polytrimethylene terephthalate (PTT), polybutylene terephthalate (PBT), polybutylene adipate terephthalate (PBAT), polybutylene terephthalate succinate (PETS), or the like. A method known in the art can be adopted as a method for producing such polyester by the polymerization of terephthalic acid and a diol compound.

FIG. 4 is a diagram showing a second example of a producing flow of terephthalic acid and polyester. In the example shown in FIG. 4, edible biomass containing polysaccharides is employed as the biomass resource, and polysaccharides are employed as the compound derived from the biomass resource. Examples of the polysaccharides can include cellulose, starch, hemicellulose, and pectin. The edible biomass containing polysaccharides is, for example, edible biomass containing starch, one of the polysaccharides (starch-based edible biomass).

Examples of the starch-based edible biomass can include, but are not particularly limited to, maize, sweet potato, rice, potato, wheat, barley, and tapioca. Only any one type of starch-based edible biomass described above may be employed, or two or more types thereof may be employed. For enhancing a hydrolysis reaction rate, it is preferred that the starch-based edible biomass should be gelatinized by the addition of water and heating.

In the example shown in FIG. 4, starting from step 200, in step 201, polysaccharides contained in edible biomass are hydrolyzed into monosaccharides. Although the polysaccharides can directly be utilized as a raw material for the microbe, it is preferred to hydrolyze the polysaccharides into monosaccharides, which are then added to a medium, for accelerating a p-tolualdehyde production rate at which the microbe according to the present invention produces p-tolualdehyde. Oligosaccharides may be contained after hydrolysis of the starch-based edible biomass.

The hydrolysis of the polysaccharides into monosaccharides may be hydrolysis with an acid such as hydrochloric acid, sulfuric acid, or phosphoric acid or may be hydrolysis with an enzyme produced by the microbe. The enzyme produced by the microbe is amylase or the like. The amylase to be employed in preparing the glucose used in the present invention from the starch-based edible biomass desirably includes at least one type such as liquefying amylase ($\alpha$-amylase), saccharifying amylase ($\beta$-amylase), pullulanase, or glucoamylase. pH or a temperature appropriate for enzyme reaction can be selected depending on the type of the enzyme. The microbe that produces amylase is not limited, and, for example, a microbe of the genus *Aspergillus*, the genus *Bacillus*, or the genus *Pseudomonas* can be employed. The hydrolysis may be carried out in a vessel different from the reaction vessel or may be carried out in the reaction vessel. In the case of carrying out hydrolysis in the reaction vessel, the enzyme such as amylase can be added to a medium for microbe culture.

Step 202 and subsequent steps are the same as the treatments in step 101 and subsequent steps shown in FIG. 2, so that the description is omitted here. In step 202, the microbe that produces the enzyme such as amylase may be added when the edible biomass is added to a culture apparatus. The microbe that produces the enzyme such as amylase may be cultured together with a microbe that forms p-tolualdehyde from saccharides.

Figure 5:
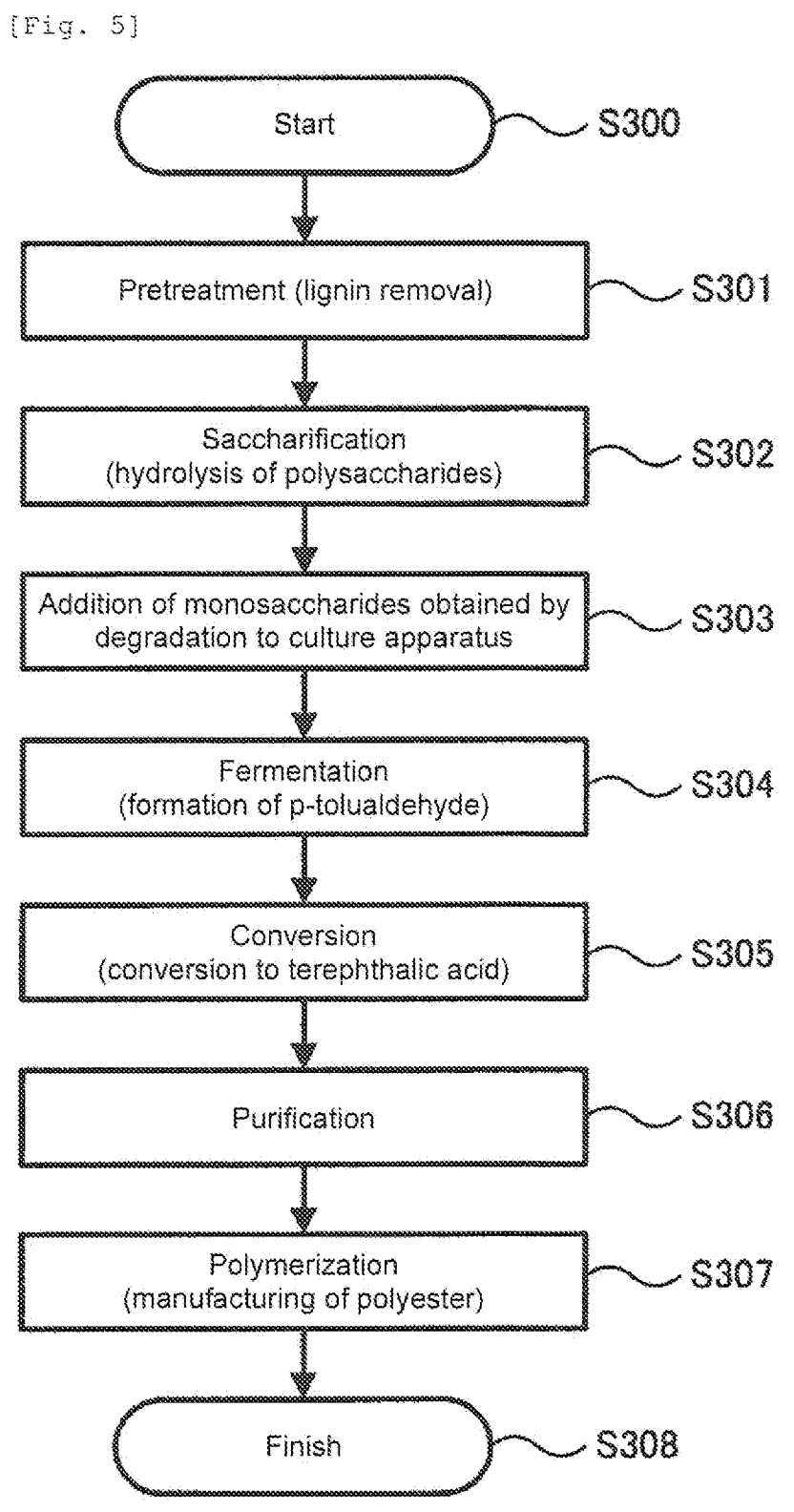

FIG. 5 is a diagram showing a third example of a producing flow of terephthalic acid and polyester. In the example shown in FIG. 5, inedible biomass is employed as the biomass resource. Unlike edible biomass, the inedible biomass is biomass that cannot be eaten. Examples of the inedible biomass can include, but are not particularly limited to, wood biomass and grass biomass. Examples of the wood biomass can include wood of softwood such as pine, cryptomeria, fir, spruce, Douglas fir, and radiata pine, and hardwood such as Japanese beech, kava, Japanese alder, maple, eucalyptus, poplar, acacia, lauan, aspen, and gum. Examples of the grass biomass can include kenaf, Manila hemp, corn stover, corn cob, bamboo, bagasse, rice straw, chaff, straw, cotton linter, reed, flax, *Erianthus, Broussonetia kazinoki* x *papyrifera*, oriental paperbush, a soybean residue, and a sweet potato stem and leaf. The inedible biomass is not limited by the employment of only one type, and plural types thereof may be employed, as in edible biomass.

In the case of employing inedible biomass as a raw material, wood or the like is not employed as it is, and is desirably employed in a physically homogenized state. This is because the penetration of a chemical is facilitated in using the chemical to decrease the content of lignin bound with, for example, cellulose, one of the polysaccharides that constitute the wood or the like.

In the example shown in FIG. 5, starting from step 300, in step 301, inedible biomass is subjected to pretreatment.

In the pretreatment, the wood biomass is mechanically homogenized into a size of 2 to 3 cm with a thickness of approximately 5 mm and thereby chipped into wood chips. Also, paper, waste paper, pulp, or the like can be used as a raw material. Paper, waste paper, or pulp produced by a method known in the art such as a chemical pulping method, a mechanical pulping method, or a semichemical pulping method can be used (see, for example, Sambrook, J et al., Molecular Cloning 2nd ed., 9.47-9.58, Cold Spring Harbor Lab. Press (1989)). The pulp is desirably rich in cellulose and hemicellulose and may contain lignin.

In the pretreatment, the penetration of a chemical can be facilitated by increasing a specific surface area by the chipping as described above. Any of other methods can be adopted as long as a lignin content can be decreased. For example, a method for producing chemical pulp known in the art can be used (see, for example, Pulp and Paper Manufacturing Technology Series, Vol. 1 Kraft Pulp, Vol. 2 Mechanical Pulp, Japan Technical Association Of The Pulp And Paper Industry).

The chemical to be employed in the pretreatment may be any chemical as long as a lignin content can be decreased. For example, sodium hydroxide, sodium sulfide, sodium sulfite, calcium sulfite, ozone, oxygen, chloride, hypochlorous acid, hydrogen peroxide, chloride dioxide, or a combination of at least two of them can be employed.

In the pretreatment, a method of treating inedible biomass at a high temperature and a high pressure in the presence or absence of a chemical may be adopted. This is because the separation and recovery of lignin are improved. The separation and recovery rate of lignin may be enhanced by adding a chemical having a quinone structure, such as anthraquinone, or a surfactant at the same time with pretreatment.

Next, in step 302, polysaccharides contained in inedible biomass are hydrolyzed into monosaccharides, as in the edible biomass containing polysaccharides shown in FIG. 4. The inedible biomass can also be hydrolyzed using an acid such as hydrochloric acid, sulfuric acid, or phosphoric acid. The hydrolysis may be performed with an enzyme produced by a microbe. For the inedible biomass, a microbe that produces an enzyme such as cellulase, hemicellulase, or ligninolytic enzyme as the enzyme can be used.

The hydrolysis may be carried out in a vessel different from the reaction vessel or may be carried out in the reaction vessel. In the case of carrying out hydrolysis in the reaction vessel, the enzyme such as cellulase, hemicellulase, or ligninolytic enzyme can be added to a medium for microbe culture. Only one type of enzyme described above may be added, or two or more types thereof may be added.

Step 303 and subsequent steps are the same as the treatments in step 101 and subsequent steps shown in FIG. 2 and step 202 and subsequent steps shown in FIG. 4, so that the description is omitted here. In step 303, the microbe that produces the enzyme such as cellulase, hemicellulase, or ligninolytic enzyme may be added when the inedible biomass is added. The microbe that produces the enzyme such as cellulase, hemicellulase, or ligninolytic enzyme may be cultured together with a microbe that forms p-tolualdehyde from saccharides.

Examples of the microbe that produces cellulase can include a bacterium such as *Acetobacter xylinum, Cellulomonas fimi*, and *Clostridium thermocellum*; and a filamentous fungus such as *Aspergillus aculeatus, Aspergillus niger, Humicola grisea, Humicola insolens, Trichoderma reesei*, and *Trichoderma viridie*. Cellulase produced by such a microbe can also be used as the enzyme.

Examples of the enzyme that constitutes the cellulase can include endoglucanase, cellobiohydrolase, cellobiose dehydrogenase, and A-glucosidase. The enzyme may be constituted by only one type thereof or may be constituted by two or more types thereof.

Commercially available cellulase Cellic Ctec3 (manufactured by Novozymes A/B) or Accellerase (DuPont Industrial Biosciences) can be used as the cellulase.

It is desirable that the hemicellulase should mainly contain xylanase when the inedible biomass is hardwood or grass inedible biomass. It is desirable that the hemicellulase should mainly contain mannase when the inedible biomass is softwood.

Basidiomycete-derived manganese peroxidase, lignin peroxidase, laccase, versatile peroxidase, or the like can be used as the ligninolytic enzyme. In the case of using manganese peroxidase, lignin peroxidase, or versatile peroxidase, it is desirable to add hydrogen peroxide, for efficiently performing enzyme reaction.

In the present specification, the term "at least 90% sequence identity" means the sequence identity to the whole sequence of interest is 90% or higher, preferably 91% or higher, more preferably 92% or higher, further preferably 93% or higher, still more preferably 94% or higher, particularly preferably 95% or higher, particularly more preferably 98% or higher, most preferably 1001 identity.

In the present specification, the term "sequence identity" means the degree of similarity between amino acid sequences (which is determined by the matching between a query sequence and another sequence, preferably, of the same type (protein sequence)). Examples of a preferred computer program method for calculating and determining the "sequence identity" can include, but are not limited to, GCG BLAST (basic local alignment search tool, (Altschul et al., J. Mol. Biol. 1990, 215: 403-410; Altschul et al., Nucleic Acids Res. 1997, 25: 3389-3402; and Devereux et al., Nucleic Acid Res. 1984, 12: 387), BLASTN 2.0 (Gish W., http://blast.wustl.edu, 1996-2002), and FASTA (Pearson and Lipman, Proc. Natl. Acad. Sci. USA 1988, 85: 2444-2448).

Example 1

*Mycoacia uda* (ATCC76971) was cultured in the presence of edible biomass rich in saccharides to form p-tolualdehyde. Then, terephthalic acid and polyester were produced by chemical synthesis.

(Preculture)

When an isolated microbe is inoculated to a large volume of a medium from the start, its inductive phase becomes long and requires a time for the proliferation of the microbe. Therefore, the microbe is first inoculated to a small amount of a medium, and after proliferation, the medium volume is increased in stages. The operation of inoculating a microbe to a small amount of a medium where the microbe is allowed to proliferate, before inoculation to a large volume of a medium is preculture.

The microbe used was *Mycoacia uda* (ATCC76971) and was cultured at a temperature of 26° C. for 1 week (7 days) in potato dextrose agar (PDA) medium as preculture. Then, the microbial cells were punched at 10 locations with a cork borer having a diameter of 7 mm and inoculated to three 300 mL Erlenmeyer flasks containing 100 mL of YM liquid medium (0.3% yeast extract, 0.3% malt extract, 1% glucose, 0.5% peptone, pH 6.2) sterilized (121° C., 20 min) in an autoclave. Then, preculture is performed with stirring of the medium for 7 days in a shaker (26° C., 100 rpm).

(Main Culture)

The culture solution after preculture was filtered through Miracloth (manufactured by Merck KGaA), and the obtained microbial cells were homogenized together with 100 mL of sterile water in a Waring blender. The homogenate of the microbial cells was cultured at a temperature of 26° C. for 2 weeks in a 3 L jar fermenter (manufactured by ABLE Corp.) using a medium containing 5% waste molasses and a yeast nitrogen base (amino acid-free) as a nitrogen source.

(Extraction and Purification of p-Tolualdehyde)

The culture solution after main culture was subjected to the extraction of p-tolualdehyde with an essential oil testing apparatus (which abides by the Japanese Pharmacopoeia 16th Edition, manufactured by Sibata Scientific Technology Ltd.). The method for extracting p-tolualdehyde abided by the Japanese Pharmacopoeia 16th Edition except that 2 mL of toluene was employed instead of xylene in a graduated tube of an analyzer. The extracted p-tolualdehyde contains toluene. Hence, in order to separate toluene, the toluene was distilled off under reduced pressure (vacuum distillation) using a rotary evaporator (manufactured by Buchi). Further, a mixed liquid of hexane and ethyl acetate mixed at 9:1 was used as a developing solvent, and p-tolualdehyde was purified by silica gel chromatography.

(Oxidation of p-Tolualdehyde into Terephthalic Acid)

Terephthalic acid is produced by the oxidation of p-tolualdehyde. Hence, the purified p-tolualdehyde was oxidized, and a method described in Japanese unexamined Patent Application Publication No. 51-86437 was adopted as the oxidation method. Specifically, the continuous oxidation of p-tolualdehyde was performed in a continuous oxidation reaction apparatus that was equipped with a reflux condenser, a stirring device, and a heating device and had a titanium pressure-resistant reactor (capacity: 2.5 L) having a raw material injection port, a raw material gas inlet, a gas outlet, and a reaction product outlet, and two reaction product receivers connected in series to the reaction product outlet.

The reactor was charged in advance with a predetermined amount of acetic acid (containing 5 wt % moisture) containing a metal catalyst and a bromine compound, pressurized to approximately 1 MPa with nitrogen, and then warmed to 210° C. After warming to 210° C., p-tolualdehyde and a reaction solution consisting of acetic acid (moisture content: 0.03 wt %) containing 0.0283 wt % cobalt as a catalyst, 0.0567 wt % manganese, and 0.121 wt % bromine were continuously supplied thereto at a ratio of 225 g/hr of p-tolualdehyde and 1120 g/hr of acetic acid in terms of a supply rate under a condition of approximately 1.8 MPa. The acetic acid containing cobalt, manganese, and bromine was made using cobalt acetate tetrahydrate, manganese acetate, and tetrabromoethane.

The reaction product was continuously discharged in a slurry state from the reactor and filtered. Then, the cake was washed twice with acetic acid and twice with water and dried to obtain terephthalic acid. The yield of the terephthalic acid thus obtained was calculated and was consequently 5.2% of saccharides contained in the waste molasses. The yield is a value indicated in percentage which was obtained by multiplying the ratio of the amount of the actually obtained terephthalic acid (yield amount) to the maximum amount of theoretically obtainable terephthalic acid (theoretical yield amount) by 100.

(Preparation of Dimethyl Terephthalate)

Polyethylene terephthalate (PET), a polymer belonging to the polyester family, is produced via dimethyl terephthalate from terephthalic acid.

105 g of the biomass resource-derived terephthalic acid obtained as described above, 200 g of methanol, 15 mL of 98 wt % sulfuric acid, and 2.25 g of copper(II) sulfate pentahydrate were added to a 500 mL autoclave, and esterification reaction was performed at 110° C. at 1.5 MPa for 1 hour. The reaction product was collected by filtration, and esterification reaction was performed again under the same conditions as above. Then, the reaction product was collected by filtration and repetitively washed with methanol. Dimethyl terephthalate was thereby obtained at a yield of 87 mol %. 0.018 wt % sodium carbonate was added to this dimethyl terephthalate, and simple distillation was performed at 185° C. at 56 hPa to obtain biomass resource-derived dimethyl terephthalate.

(Preparation of Polyethylene Terephthalate (PET))

1 wt % metal sodium was added to biomass resource-derived ethylene glycol (manufactured by India Glycols Ltd), and the mixture was refluxed for 1 hour, followed by purification by distillation. 15.5 g of the biomass resource-derived dimethyl terephthalate obtained as described above, 11.8 g of the ethylene glycol thus purified, 0.025 g of calcium acetate, and 0.01 g of antimony triozide were weighed into a 100 mL round-bottomed flask, and a Claisen tube and an air cooler were attached to this round-bottomed flask. A nitrogen gas was introduced into the reaction system to remove air. Then, the contents were melted by heating to 180° C. A capillary tube was inserted thereto, and a nitrogen gas was introduced into the reaction system. Then, methanol was distilled off for 1 hour.

Heating was continued at 200° C. for 2 hours to eliminate methanol. Then, an excess of ethylene glycol was distilled off by warming to 220° C. After a lapse of 20 minutes from warming to 20° C., the temperature was elevated to 280° C. and maintained for 15 minutes. Then, a vacuum adaptor was attached thereto, and the pressure was gradually reduced to 0.4 hPa. 3 hours later, the reactor was cooled while a nitrogen gas was introduced. After cooling, vacuum drying was performed at 150° C. for 12 hours.

The dried product was melted at a spinning temperature of 285° C., discharged from a spinneret having a pore diameter of 0.18 me, and taken up on a take-up roller to obtain an undrawn yarn. The obtained undrawn yarn was drawn in a hot-roll drawing machine and heat-treated to obtain a PET fiber. The obtained biomass resource-derived PET had favorable polymer characteristics, spinning stability, and dye exhaustion cate.

Example 2

Terephthalic acid and polyester were produced using starch-based edible biomass. In the case of using starch-based edible biomass, it is desirable to hydrolyze polysaccharides into monosaccharides by saccharification treatment. Therefore, saccharification treatment was performed.

(Enzymatic Saccharification of Starch)

The starch-based edible biomass used was corn starch (manufactured by Oji Cornstarch Co., Ltd.). Corn starch was added at a concentration of 30 wt % to ion exchange water and sterilized in an autoclave (121° C., 20 min). Then, the mixture was cooled to 90° C. 0.2 wt % thermostable α-amylase (Termamyl 120, manufactured by Novozymes A/S) was added thereto, and the mixture was reacted with stirring for 3 hours. Then, the reaction mixture was cooled to 60° C. After cooling, 0.35 wt % glucoamylase (Allcoholase II L400, manufactured by Alltech) was added thereto with stirring, and the mixture was reacted for 2 hours to perform the saccharification of the starch.

After saccharification, the starch thus enzymatically saccharified was added at a glucose concentration of 10 wt % instead of waste molasses in the main culture of Example 1. Terephthalic acid and polyester were produced in the same manner as in Example 1 except for the procedure described above. The yield of the terephthalic acid thus obtained was 5.1% of the added starch. The obtained biomass resource-derived PET had favorable polymer characteristics, spinning stability, and dye exhaustion rate.

Example 3

Terephthalic acid and polyester were produced using inedible biomass. In the case of using inedible biomass, a lignin content was decreased by pretreatment and saccharification treatment, and polysaccharides were hydrolyzed into monosaccharides.

Hardwood pulp (10 wt %) after oxygen delignification in which a lignin content was decreased using the chemical or physical treatment or the ligninolytic enzyme mentioned above was added instead of waste molasses in the main culture of Example 1. Also, commercially available cellulase (Cellic CTec3, manufactured by Novozymes A/S) was added such that the enzyme activity in a medium was 10 U/mL. 1 U (enzyme unit) is the amount of an enzyme that catalyzes change in 1 μmol of a substrate per minute under fixed conditions. Terephthalic acid and polyester were produced in the same manner as in Example 1 except for the procedure described above. The yield of the terephthalic acid thus obtained was 3.8% of the hardwood pulp after oxygen delignification. The obtained biomass resource-derived PET had favorable polymer characteristics, spinning stability, and dye exhaustion rate.

Example 4

Terephthalic acid and polyester were produced from a biomass resource-derived raw material p-methylacetophenone.

Preculture was performed in the same manner as in Example 1, and biomass resource-derived p-methylacetophenone was added at a concentration of 1 wt % in a medium in main culture. The biomass resource-derived p-methylacetophenone was obtained by the oxidation of citral obtained from a biomass resource lemon. The oxidation of citral was performed by a method described in the document (Ueno et al., Formation Mechanism of p-Methylacetophenone from Citral via a tert-Alkoxy Radical Intermediate. J. Agric. Food Chem., 52, 5677-5684 (2004)). As a result, the yield of terephthalic acid was 1.5% of the added citral. The obtained biomass resource-derived PET had favorable polymer characteristics, spinning stability, and dye exhaustion rate.

In this context, although there is no document stating that terephthalic acid is produced from a biomass resource and its yield is calculated, there are found a document that discloses a yield in a method for producing p-tolualdehyde from a biomass resource-derived substance (patent document 3 described above) and a document that discloses a yield in a method for producing terephthalic acid from p-tolualdehyde (Japanese unexamined Patent Application Publication No. 51-86437). According to these documents, the overall yield for obtaining terephthalic acid from a biomass resource is calculated and is consequently approximately 3.8 to 4.9%.

The method of the present invention had a yield of 1.5 to 5.2% as shown in Examples 1 to 4, and was thus found to be able to produce terephthalic acid at a yield almost equivalent to the case of producing terephthalic acid via p-tolualdehyde from a biomass resource-derived substance, though not employing a microbe.

Example 5

Benzaldehyde dehydrogenase gene, toluate methylmonooxygenase gene, 4-carboxybenzyl alcohol dehydrogenase gene, and 4-carboxybenzaldehyde dehydrogenase gene for basidiomycete (*Mycoacia uda*) were prepared.

(5-1) Preparation of Benzaldehyde Dehydrogenase Gene for Basidiomycete (*Mycoacia uda*)

The base sequence and amino acid sequence of *Pseudomonas putida*-derived benzaldehyde dehydrogenase gene are known in the art (accession No: AAN67564). In order to allow basidiomycete to efficiently express benzaldehyde dehydrogenase (polypeptide consisting of the amino acid sequence represented by SEQ ID NO: 19), the base sequence of the *Pseudomonas putida*-derived benzaldehyde dehydrogenase gene was optimized using geneious prime (manufactured by Biomatters) on the basis of the frequency of codon usage in basidiomycete, followed by the chemical synthesis of DNA, which was designated as MuBZDH. MuBZDH was cloned into pUC18 (manufactured by Takara Bio Inc.), which was designated as pMuBZDH.

(5-2) Preparation of Toluate Methylmonooxygenase Gene, 4-Carboxybenzyl Alcohol Dehydrogenase Gene, and 4-Carboxybenzaldehyde Dehydrogenase Gene for Basidiomycete (*Mycoacia uda*)

Toluate methylmonooxygenase gene for basidiomycete (*Mycoacia uda*), 4-carboxybenzyl alcohol dehydrogenase gene for basidiomycete (*Mycoacia uda*), and 4-carboxybenzaldehyde dehydrogenase gene for basidiomycete (*Mycoacia uda*) were prepared in the same manner as the preparation method described in the section (5-1) described above. The nucleotide sequences and amino acid sequences of *Comamonas testosteroni*-derived toluate methylmonooxygenase gene (tsaMB), 4-carboxybenzyl alcohol dehydrogenase gene (tsaC), and 4-carboxybenzaldehyde dehydrogenase gene (tsaD) are known in the art [document (Junker F, Kiewitz R, Cook AM. Characterization of the p-toluenesulfonate operon tsaMBCD and tsaR in *Comamonas testosteroni* T-2. J Bacteriol. 179 (3). 919-927. 1997)]. In order to allow basidiomycete to efficiently express toluate methylmonooxygenase (polypeptide consisting of the amino acid sequence represented by SEQ ID NO: 20), 4-carboxybenzyl alcohol dehydrogenase (polypeptide consisting of the amino acid sequence represented by SEQ ID NO: 21), and 4-carboxybenzaldehyde dehydrogenase (polypeptide consisting of the amino acid sequence represented by SEQ ID NO: 22), the nucleotide sequences of the *Comamonas testosteroni*-derived toluate methylmonooxygenase gene (tsaMB), 4-carboxybenzyl alcohol dehydrogenase gene (tsaC), and 4-carboxybenzaldehyde dehydrogenase gene (tsaD) were optimized using geneious prime (manufactured by Biomatters) on the basis of the frequency of codon usage in basidiomycete, followed by the chemical synthesis of DNA. The toluate methylmonooxygenase-encoding DNA optimized for basidiomycete was designated as MutsaMB, the 4-carboxybenzyl alcohol dehydrogenase-encoding DNA optimized for basidiomycete was designated as MutsaC, and the 4-carboxybenzaldehyde dehydrogenase-encoding DNA optimized for basidiomycete was designated as MutsaD. MutsaMB, MutsaC, and MutsaD were each cloned into pUC18 (manufactured by Takara Bio Inc.), which was designated as pMutsaMB, pMutsaC, and pMutsaD, respectively.

Example 6

MuBZDH, MutsaMB, MutsaC, and MutsaD expression vectors were constructed using a promoter and a 3'-terminal region of basidiomycete (*Mycoacia uda*)-derived glyceraldehyde-3-phosphate dehydrogenase gene (gpd).

(6-1) Construction of Benzaldehyde Dehydrogenase (MuBZDH) Expression Vector Using a Promoter and a 3'-Terminal Region of Basidiomycete (*Mycoacia uda*)-Derived Glyceraldehyde-3-Phosphate Dehydrogenase (GPD) Gene A MuBZDH expression vector for *Mycoacia uda* was constructed using double joint PCR, a method known in the art. Specifically, the construction was performed in accordance with a method described in the document (Yu, J. H., Hamari, Z., Han, K. H., Seo, J. A., Reyes-Dominguez, Y., Scazzocchio, "C. Double-joint PCR: a PCR-based molecular tool for gene manipulations in filamentous fungi." Fungal Genetics and Biology. 41 (11). 973-981. (2004)).

For the expression of the benzaldehyde dehydrogenase gene (MuBZDH) prepared in (5-1) above in basidiomycete (*Mycoacia uda*), a promoter region of *M. uda* glyceraldehyde-3-phosphate dehydrogenase (GPD) gene known to be constitutively expressed was used as a promoter. In order to obtain the promoter region of the *H. uda* GPD gene, PCR reaction was performed with the genomic DNA of *M. uda* as a template using a primer consisting of the nucleotide sequence represented by SEQ ID NO: 1 and a primer consisting of the nucleotide sequence represented by SEQ ID NO: 2. The enzyme used in PCR was KOD plus sold by Toyobo Co., Ltd., and the PCR reaction was performed under a condition of 30 cycles each involving 94° C. for 1 minute, 60° C. for 1 minute, and 72° C. for 2 minutes. A 1 kbp DNA fragment amplified through the PCR reaction was purified using QIAquick PCR Purification Kit (manufactured by Qiagen N.V.).

Next, PCR reaction was performed with the pMuBZDH prepared in (5-1) above (i.e., the plasmid containing the nucleotide sequence of the benzaldehyde dehydrogenase gene (MuBZDH) optimized for basidiomycete) as a template using a primer consisting of the nucleotide sequence represented by SEQ ID NO: 3 and a primer consisting of the nucleotide sequence represented by SEQ ID NO: 4. The enzyme used in PCR was KOD plus sold by Toyobo Co., Ltd., and the PCR reaction was performed under a condition of 30 cycles each involving 94° C. for 1 minute, 60° C. for 1 minute, and 72° C. for 2 minutes. A DNA fragment amplified through the PCR reaction was purified using QIAquick PCR Purification Kit (manufactured by Qiagen N.V.).

For the stabilization of MuBZDH expression, a 3'-terminal region (0.8 kbp) of the *M. uda* GPD gene was employed. In order to amplify this region, PCR reaction was performed with the genomic DNA of *M. uda* as a template using a primer consisting of the nucleotide sequence represented by SEQ ID NO: 5 and a primer consisting of the nucleotide sequence represented by SEQ ID NO: 6. The enzyme used in PCR was KOD plus sold by Toyobo Co., Ltd., and the PCR reaction was performed under a condition of 30 cycles each involving 94° C. for 1 minute, 60° C. for 1 minute, and 72° C. for 1 minute. A 0.8 kbp DNA fragment obtained was purified using QIAquick PCR Purification Kit (manufactured by Qiagen N.V.).

Subsequently, PCR reaction was performed using (1) the *Mycoacia uda* glyceraldehyde-3-phosphate dehydrogenase gene (gpd) promoter region, (2) the benzaldehyde dehydrogenase gene optimized for basidiomycete, and (3) the *Mycoacia uda* GPD gene 3'-terminal region amplified by PCR as described above. The enzyme used in PCR was KOD plus sold by Toyobo Co., Ltd., and the PCR reaction was performed under a condition of 30 cycles each involving 94° C. for 1 minute, 60° C. for 10 minutes, and 72° C. for 5 minutes. A DNA fragment after PCR was purified using QIAquick PCR Purification Kit (manufactured by Qiagen N.V.).

Subsequently, PCR reaction was performed with the purified DNA fragment after PCR as a template using a primer consisting of SEQ ID NO: 1 and a primer consisting of the nucleotide sequence represented by SEQ ID NO: 6. The PCR enzyme used was ROD plus sold by Toyobo Co., Ltd., and the PCR reaction was performed under a condition of 30 cycles each involving 94° C. for 1 minute, 60° C. for 1 minute, and 72° C. for 5 minutes. A DNA fragment after PCR was purified using QIAquick PCR Purification Kit (manufactured by Qiagen N.V.). Cloning was performed using TOPO TA Cloning Kit (manufactured by Invitrogen Corp.). The resulting vector was designated as pGPDMuBZDH. In order to determine a nucleotide sequence, the obtained DNA fragment was subjected to PCR reaction using a nucleotide sequence analysis reagent produced by Applied Biosystems Inc., and the reaction product was analyzed using ABI PRISM 310 automated nucleotide sequence determination apparatus, a DNA sequencer produced by Applied Biosystems Inc.

(6-2) Construction of Toluate Methylmonooxygenase Gene Expression Vector, 4-Carboxybenzyl Alcohol Dehydrogenase Gene Expression Vector, and 4-Carboxybenzaldehyde Dehydrogenase Gene Expression Vector Using Promoter and 3'-Terminal Region of Basidiomycete (*Mycoacia uda*)-Derived Glyceraldehyde-3-Phosphate Dehydrogenase Gene (gpd)

The promoter of the basidiomycete (*Mycoacia uda*)-derived GPD gene was linked to the 5' end of each of the toluate methylmonooxygenase gene (MutsaMB) for basidiomycete (*Mycoacia uda*), the 4-carboxybenzyl alcohol dehydrogenase gene (MutsaC) for basidiomycete (*Mycoacia uda*), and the 4-carboxybenzaldehyde dehydrogenase gene (MutsaD) for basidiomycete (*Mycoacia uda*), and the 3'-terminal region of the basidiomycete (*Mycoacia uda*)-derived GPD gene was linked to the 3' end of each of these genes to construct a toluate methylmonooxygenase gene expression vector (pGPDMutsaMB), a 4-carboxybenzyl alcohol dehydrogenase gene expression vector (pGPDMutsaC), and a 4-carboxybenzaldehyde dehydrogenase gene expression vector (pGPDMutsaD), respectively. Fox the construction of these gene expression vectors, PCR reaction was performed using the vector (pMutsaMB) containing the toluate methylmonooxygenase gene, the vector (pMutsaC) containing the 4-carboxybenzyl alcohol dehydrogenase gene, and the vector (pMutsaD) containing the 4-carboxybenzaldehyde dehydrogenase gene, respectively, as a template instead of pMuBZDH in the method for preparing pGPDMuBZDH in (6-1) above.

In the process of constructing the toluate methylmonooxygenase gene expression vector (pGPDMutsaMB), a primer consisting of the nucleotide sequence represented by SEQ ID NO: 1 and a primer consisting of the nucleotide sequence represented by SEQ ID NO: 7 were used in the amplification of the *Mycoacia uda* gpd promoter; a primer consisting of the nucleotide sequence represented by SEQ ID NO: 8 and a primer consisting of the nucleotide sequence represented by SEQ ID NO: 9 were used in the amplification of the toluate methylmonooxygenase gene; a primer consisting of the nucleotide sequence represented by SEQ ID NO: 6 and a primer consisting of the nucleotide sequence represented by SEQ ID NO: 10 were used in the amplification of the 3'-terminal region (0.8 kbp) of the *M. uda* gpd gene; and a primer consisting of the nucleotide sequence represented by SEQ ID NO: 1 and a primer consisting of the nucleotide sequence represented by SEQ ID NO: 6 were used in the amplification of GPDMutsaMB. The PCR reaction conditions except for the primers are the same as in (6-1) above. A DNA fragment after PCR reaction was purified using QIAquick PCR Purification Kit (manufactured by Qiagen N.V.) and then cloned using TOPO TA Cloning Kit (manufactured by Invitrogen Corp.). The resulting vector was designated as pGPDMutsaMB.

In the process of constructing the 4-carboxybenzyl alcohol dehydrogenase gene expression vector (pGPDMutsaC), a primer consisting of the nucleotide sequence represented by SEQ ID NO: 1 and a primer consisting of the nucleotide sequence represented by SEQ ID NO: 11 were used in the amplification of the *Mycoacia uda* gpd promoter; a primer consisting of the nucleotide sequence represented by SEQ ID NO: 12 and a primer consisting of the nucleotide sequence represented by SEQ ID NO: 13 were used in the amplification of the 4-carboxybenzyl alcohol dehydrogenase gene; a primer consisting of the nucleotide sequence represented by SEQ ID NO: 6 and a primer consisting of the nucleotide sequence represented by SEQ ID NO: 14 were used in the amplification of the 3'-terminal region (0.8 kbp) of the *M. uda* gpd gene; and a primer consisting of the nucleotide sequence represented by SEQ ID NO: 1 and a primer consisting of the nucleotide sequence represented by SEQ ID NO: 6 were used in the amplification of GPDMutsaC. The PCR reaction conditions except for the primers are the same as in (6-1) above. A DNA fragment after PCR reaction was purified using QIAquick PCR Purification Kit (manufactured by Qiagen N.V.) and then cloned using TOPO TA Cloning Kit (manufactured by Invitrogen Corp.). The resulting vector was designated as pGPDMutsaC.

In the process of constructing the 4-carboxybenzaldehyde dehydrogenase gene expression vector (pGPDMutsaD), a primer consisting of the nucleotide sequence represented by SEQ ID NO: 1 and a primer consisting of the nucleotide sequence represented by SEQ ID NO: 15 were used in the amplification of the *Mycoacia uda* gpd promoter; a primer consisting of the nucleotide sequence represented by SEQ ID NO: 16 and a primer consisting of the nucleotide sequence represented by SEQ ID NO: 17 were used in the amplification of the 4-carboxybenzaldehyde dehydrogenase gene; a primer consisting of the nucleotide sequence represented by SEQ ID NO: 6 and a primer consisting of the nucleotide sequence represented by SEQ ID NO: 18 were used in the amplification of the 3'-terminal region (0.8 kbp) of the *M. uda* GPD gene; and a primer consisting of the nucleotide sequence represented by SEQ ID NO: 1 and a primer consisting of the nucleotide sequence represented by SEQ ID NO: 6 were used in the amplification of GPDMutsaD. The PCR reaction conditions except for the primers are the same as in (6-1) above. A DNA fragment after PCR reaction was purified using QIAquick PCR Purification Kit (manufactured by Qiagen N.V.). Cloning was performed using TOPO TA Cloning Kit (manufactured by Invitrogen Corp.). The resulting vector was designated as pGPDHutsaD.

Example 7

A transformed strain of *Mycoacia uda* for biosynthesizing terephthalic acid from a biomass resource was made.

(7-1) Culture of Mycelium 100 mL of SHY medium (1% sucrose, 18 malt extract, 0.4% yeast extract) was dispensed to a 500 mL Erlenmeyer flask containing approximately 30 glass beads having a diameter of approximately 6 mm, and sterilized. Then, a plate agar medium of *H. uda* (ATCC76971) was punched into an agar piece of 5 mm in a diameter with a cork borer, and the agar piece was inoculated to the SKY medium and statically cultured at 26° C. for 7 days (preculture). In order to chop hyphae, the cultures were shaken once or twice a day. Next, 200 mL of SHY medium was dispensed to a 1 L Erlenmeyer flask, and a rotator was placed therein. After sterilization, the precultured hyphae were collected by filtration through a nylon mesh (pore diameter: 30 μm), and the whole amount was inoculated to the medium and cultured at 26° C. The hyphae were chopped by stirring for 2 hours per day with a stirrer. This culture was performed for 7 days.

(7-2) Preparation of Protoplast

The liquid-cultured hyphae were collected by filtration through a nylon mesh (pore diameter: 30 μm) and washed with an osmoregulatory solution (0.5 M $MgSO_4$, 50 mL of a malate buffer (pH 5.6)). Next, the hyphae were suspended in a cell wall-degrading enzyme solution (1 mL per 100 mg of wet microbial cells) [5 mg of cellulase ONOZUKA RS (manufactured by Yakult Honsha Co., Ltd.) and 10 mg of Yatalase (manufactured by Takara Shuzo Co., Ltd.) dissolved in 1 mg of the osmoregulatory solution] and incubated at 26° C. for 3 hours with mild shaking to liberate protoplasts.

(7-3) Purification of Protoplast

Hypha fragments were removed from the enzyme reaction solution containing the protoplasts through a nylon mesh (pore diameter: 30 μm). Then, in order to enhance the recovery rate of the protoplasts, the hypha fragments remaining on the nylon mesh and the protoplasts were washed once with the osmoregulatory solution. The obtained protoplast suspension was centrifuged (1,000 g, 5 min), and the supernatant was removed. The protoplasts were resuspended in a 20 mM MOPS buffer solution (pH 6.3) containing 4 mL of 1 M sucrose, then repetitively subjected to a centrifugation operation, and washed twice with the 1 M sucrose solution. The precipitate was suspended in 500 μL of a solution of 40 mM calcium chloride added to a 20 mM MES buffer solution (pH 6.4) containing 1 M sorbitol to prepare a protoplast suspension. This suspension was preserved at 4° C. The protoplast concentration was determined by direct counting using a counting chamber. All the centrifugation operations were performed at 1,000 g at room temperature for 5 minutes with a swing rotor.

(7-4) Transformation of *Mycoacia uda* Using Benzaldehyde Dehydrogenase Gene Expression Vector (pGPDMuBZDH), Toluate Methylmonooxygenase Gene Expression Vector (pGPDMutsaMB), 4-Carboxybenzyl Alcohol Dehydrogenase Gene Expression Vector (pGPDMutsaC), and 4-Carboxybenzaldehyde Dehydrogenase Gene Expression Vector (pGPDMutsaD)

2 μg each of the benzaldehyde dehydrogenase gene expression vector (pMuBZDH), the toluate methylmonooxygenase gene expression vector (pGPDMutsaMB), the 4-carboxybenzyl alcohol dehydrogenase gene expression vector (pGPDMutsaC), and the 4-carboxybenzaldehyde dehydrogenase gene expression vector (pGPDMutsaD) constructed in (6-1) and (6-2) above and *Mycoacia uda*-derived carboxin resistance gene prepared by a method known in the art was added to 100 μL of the protoplast suspension with approximately 100 protoplasts/100 μL purified in (7-3) above, and the mixture was cooled on ice for 30 minutes. Next, an equal amount of a PEG solution (20 mM MOPS buffer solution (pH 6.4) containing 50% PEG3400) was added to the protoplast-DNA mixed solution, and the mixture was further cooled on ice for 30 minutes. Next, the mixture was solidified by gentle mixing with 10 mL minimal agar medium (agar: 1%) containing 0.5 M sucrose, and cultured at 26° C. for several days. After culture for 3 days, 10 mL of minimal agar medium containing 2 μg/mL carboxin was layered thereon, and culture was further continued. After layering, grown transformants were selected.

Example 8

The transformants obtained by transfection with the benzaldehyde dehydrogenase gene expression vector (pGPDMuBZDH), the toluate methylmonooxygenase gene expression vector (pGPDMutsaMB), the 4-carboxybenzyl alcohol dehydrogenase gene expression vector (pGPDMutsaC), and the 4-carboxybenzaldehyde dehydrogenase gene expression vector (pGPDMutsaD) using the basidiomycete (*Mycoacia uda*)-derived GPD promoter were cultured in the presence of edible biomass rich in saccharides to form terephthalic acid.

The transformants made in (7-4) above were cultured at 26° C. on potato dextrose agar medium and then preserved at 4° C. Preculture and main culture were performed in the same manner as in Example 1. Terephthalic acid contained in the culture solution of main culture was quantified by HPLC analysis in accordance with a method known in the art [document (Luo, Z., Lee, S. Biotransformation of p-xylene into terephthalic acid by engineered *Escherichia coli*. Nat Commun 6, 15689 (2017))].

As a result, the yield of terephthalic acid was 5.0% of saccharides contained in waste molasses. The obtained biomass resource-derived PET had favorable polymer characteristics, spinning stability, and stainability. On the other hand, transformants harboring only *Mycoacia uda*-derived carboxin resistance gene which were made as Comparative Example produced no terephthalic acid.

This result indicates that when a microbe expressing four types of enzymes (benzaldehyde dehydrogenase [BZDH), toluate methylmonooxygenase (TsaMB], 4-carboxybenzyl alcohol dehydrogenase [TsaC], and 4-carboxybenzaldehyde dehydrogenase (TsaD)) is cultured in the presence of a biomass resource, terephthalic acid can be produced via p-tolualdehyde from a biomass resource-derived substance.

Example 9

*Hydnophlebia chrysorhiza* was cultured in the presence of edible biomass rich in saccharides used to form p-tolualdehyde. Then, terephthalic acid and polyester were produced by chemical synthesis.

Terephthalic acid and polyester were produced with waste molasses as a raw material in the same manner as in Example 1 using *Hydnophlebia chrysorhiza* FD-282 instead of the microbe employed in Example 1 (*Mycoacia uda* ATCC76971).

As a result, the yield of terephthalic acid was 4.8% of saccharides contained in the waste molasses. The obtained biomass resource-derived PET had favorable polymer characteristics, spinning stability, and stainability.

In conclusion, the method of the present invention can produce terephthalic acid at a relatively high yield, achieves production at a mild temperature as compared with a conventional method, and can reduce the amount of energy consumption. Furthermore, the method of the present invention can produce terephthalic acid through one step by producing terephthalic acid by a small number of steps, i.e., a step of converting a biomass resource or a compound derived from the biomass resource to p-tolualdehyde with a microbe, or by biotransforming terephthalic acid from p-tolualdehyde formed in a microbe, as compared with a conventional method. Inexpensive production is achieved because an expensive furnace, fractionator, or the like required for pyrolysis is not employed. A microbe cultured and proliferated can also be provided because p-tolualdehyde and terephthalic acid are formed by microbe culture.

The present invention can provide a method for producing terephthalic acid and a method for producing polyester as well as terephthalic acid and polyester produced by these production methods.

The method for producing terephthalic acid and the method for producing polyester according to the present invention, and terephthalic acid and polyester produced by these production methods are described above in detail with reference to the embodiments mentioned above. However, the present invention is not limited by the embodiments mentioned above, and other embodiments, addition, change, deletion, and the like can be made within a range conceivable by those skilled in the art. Any aspect is included in the scope of the present invention as long as the action or effect of the present invention is exerted.

EXPLANATION OF LETTERS OR NUMERALS

10 . . . Reaction vessel
11 . . . Medium
12 . . . Stirrer
13 . . . Reservoir
14 to 16 . . . Pump

The invention claimed is:

1. A method for producing terephthalic acid, comprising:

a step of converting a biomass resource or a compound derived from the biomass resource to p-tolualdehyde with a microbe; and a step of biologically oxidizing the converted p-tolualdehyde by use of the microbe to produce terephthalic acid, wherein the microbe belongs to the family Meruliaceae.

2. The method for producing terephthalic acid according to claim 1, wherein the compound derived from the biomass resource is at least one of shikimic acid, 1-p-tolyl ethanol, p-methylacetophenone, and p-methylbenzyl alcohol.

3. The method for producing terephthalic acid according to claim 1, wherein the biomass resource is a biomass resource treated by a pretreatment step or a saccharification step, or by both the pretreatment and the saccharification steps.

4. The method for producing terephthalic acid according to claim 1, wherein the biomass resource is any one or more of edible biomass, edible biomass-derived monosaccharides or polysaccharides, inedible biomass, and inedible biomass-derived monosaccharides or polysaccharides.

5. The method for producing terephthalic acid according to claim 4, wherein the edible biomass comprises at least one type of biomass selected from maize, sweet potato, rice, potato, wheat, barley, tapioca, sugar cane, beet, molasses, and high-test molasses.

6. The method for producing terephthalic acid according to claim 4, wherein the inedible biomass comprises at least one type of biomass selected from grass-based biomass, wood-based biomass, paper, pulp, waste paper, bagasse, and corn stover.

7. The method for producing terephthalic acid according to claim 1, further comprising a step of adding at least one type of enzyme selected from amylase, cellulase, hemicellulase, and ligninolytic enzyme to a medium.

8. The method for producing terephthalic acid according to claim 1, wherein the microbe is transfected with a gene group encoding benzaldehyde dehydrogenase, toluate methylmonooxygenase, 4-carboxybenzyl alcohol dehydrogenase, and 4-carboxybenzaldehyde dehydrogenase.

9. The method for producing terephthalic acid according to claim 1, wherein the microbe is *Phlebia uda* or *Hydnophlebia chrysorhiza.*

10. A method for producing polyester, comprising a step of producing terephthalic acid according to the method of claim 1; and a step of reacting the terephthalic acid with a diol compound to produce the polyester.

11. The method for producing terephthalic acid according to claim 8, wherein the microbe is *Phlebia uda* or *Hydnophlebia chrysorhiza.*

12. A method for producing polyester, comprising a step of producing terephthalic acid according to the method of claim 3; and a step of reacting the terephthalic acid with a diol compound to produce the polyester.

13. A method for producing polyester, comprising a step of producing terephthalic acid according to the method of claim 11; and a step of reacting the terephthalic acid with a diol compound to produce the polyester.

* * * * *